United States Patent [19]

Holland et al.

[11] Patent Number: 5,143,830
[45] Date of Patent: Sep. 1, 1992

[54] PROCESS FOR THE PRODUCTION OF A POLYPEPTIDE

[76] Inventors: Ian B. Holland, 24 Woodcroft Avenue, Leicester, LE2 6HE, England; Nigel Mackman, 375 Bonair St., LaJolla, Calif. 92037; Jean-Marc Nicaud, 71, rue Vauvenargues, F-75018, Paris, France

[21] Appl. No.: 138,035
[22] PCT Filed: May 14, 1987
[86] PCT No.: PCT/GB87/00331
§ 371 Date: Feb. 26, 1988
§ 102(e) Date: Feb. 26, 1988
[87] PCT Pub. No.: WO87/06953
PCT Pub. Date: Nov. 19, 1987

[30] Foreign Application Priority Data

May 15, 1986 [GB] United Kingdom ............. 8611832

[51] Int. Cl.⁵ .............. C12N 15/62; C12N 15/63; C12N 15/09; C07H 21/04
[52] U.S. Cl. ............... 435/69.7; 435/252.3; 435/320.1; 536/27; 935/48
[58] Field of Search ............ 435/172.3, 69.1, 235, 435/320, 252.8, 849, 69.7, 172.3; 536/27; 935/38, 47, 48; 530/350

[56] References Cited

PUBLICATIONS

Felmlee et al., Jul. 1985 J. Bact. 163(1) 94–105.
Oliver D. B. et al., Jan. 1985, J. Bact. 161(1) 285–291.

*Primary Examiner*—Richard A. Schwartz
*Assistant Examiner*—John D. Ulm
*Attorney, Agent, or Firm*—Cushman, Darby & Cushman

[57] ABSTRACT

A process for the production of a polypeptide in which host cells transformed with DNA coding for a fusion protein comprising the polypeptide and a further peptide comprising a C-terminal secretion sequence are cultured to express and secrete the fusion protein. The C-terminal secretion sequence is, for example, the haemolysin C-terminal secretion sequence.

11 Claims, 18 Drawing Sheets

Fig. 3

```
                                                    10                                          20
 B  Gly Asn Ser Leu Ala Lys Asn Val Leu Ser Gly Gly Lys Gly Asn Asp Lys Leu Tyr Gly
    GGG AAT TCT CTT GCT AAA AAT GTA TTA TCC GGT GGA AAA GGT AAT GAC AAG TTG TAC GGC
     A           A                                                  C 30                                          40
    Ser Glu Gly Ala Asp Leu Leu Asp Gly Gly Glu Gly Asn Asp Leu Leu Lys Gly Gly Tyr
    AGT GAG GGA GCA GAG CTG CTT GAT GGC GGA GAA GGG AAT GAT CTT CTG AAA GGT GGA TAT
                     T

50                                      Asp 60
    Gly Asn Asp Ile Tyr Arg Tyr Leu Ser Gly Tyr Gly His His Ile Ile Asp Asp Glu Gly
    GGT AAT GAT ATT TAT CGT TAT CTT TCA GGA TAT GGC CAT CAT ATT ATT GAC GAT GAA GGG
                                                                            T

Asp                                         70                                  80
    Gly Lys Glu Asp Lys Leu Ser Leu Ala Asp Ile Asp Phe Arg Asp Val Ala Phe Lys Arg
    GGG AAA GAG GAT AAA CTC AGT TTG GCT GAT ATA GAT TTC CGG GAG GTT GCC TTC AAG CGA
             G                                   T          G   T 90                                         100
    Glu Gly Asn Asp Leu Ile Met Tyr Lys Ala Glu Gly Asn Val Leu Ser Ile Gly His Lys
    GAA GGC AAT GAC CTC ATT ATG TAT AAA GCT GAA GGT AAT GTT CTT TCC ATT GGC CAC AAA
            G           C

110                        Ile           120
    Asn Gly Ile Thr Phe Lys Asn Trp Phe Glu Lys Glu Ser Asp Asp Leu Ser Asn His Gln
    AAT GGT ATT ACA TTT AAA AAC TGG TTT GAA AAA GAG TCA GAT GAT CTC TCT AAT CAT CAG
                                                             A                C 130                                        140
    Ile Glu Gln Ile Phe Asp Lys Asp Gly Arg Val Ile Thr Pro Asp Ser Leu Lys Lys Ala
    ATA GAG CAG ATT TTT GAT AAA GAC GGC AGG GTA ATC ACA CCA GAT TCT CTT AAA AAG GCA

Leu                                 150            Ala             Asn     Leu Ala
    Phe Glu Tyr Gln Gln Ser Asn Asn Lys Val Ser Tyr Val Tyr Gly His Asp Ala Ser Thr
    TTT GAA TAT CAG CAG AGT AAT AAC AAG GTA AGT TAT GTG TAT GGA CAT GAT GCA TCA ACT
    C       C   A                       C                    A       A        T  GC

Gly             170
    Tyr Gly Ser Gln Asp Asn Leu Asn Pro Leu Ile Asn Glu Ile Ser Lys Ile Ile Ser Ala
    TAT GGC AGC CAG GAC AAT CTT AAT CCA TTA ATT AAT GAA ATC AGC AAA ATC ATT TCA GCT
         A       A   GT

190  Ala                              200
    Ala Gly Asn Phe Asp Val Lys Glu Glu Arg Ser Ala Ala Ser Leu Leu Gln Leu Ser Gly
    GCA GGT AAT TCG GAT GTT AAG GAG GAA AGA TCT GCC GCT TCT TTA TTG CAG TTG TCC GGT
                            A           G   A

210
    Asn Ala Ser Asp Phe Ser Tyr Gly Arg Asn Ser Ile Thr Leu Thr Ala Ser Ala ***
    AAT GCC AGT GAT TTT TCA TAT GGA CGG AAC TCA ATA ACT TTG ACA GCA TCA GCA TAA
```

```
A    pSF4000  __B_____E___E___Bg__ pLG570   __B_____E___E___Bg__
```

SUBCLONES OF PLG609, USING ECOR1 LINKER DNA, GENERATING
DIFFERENT READING FRAMES TO THE HAEMOLYSIN 23KD SECRETION SIGNAL

```
              ECOR1
PLG609      G  AAT  TCT  CTT

SMAI
PLG609 - 1   G  AAT  TTT  CCC  C | GGG  GAA  AAT  TCT  CTT

SMAI
PLG609 - 2   G  AAT  TTT  CCC | GG  GAA  AAT  TCT  CTT

SMAI
PLG609 - 3   G  AAT  TTC  CC | G  GGA  AAT  TCT  CTT

BAMH1
PLG609 - 4   G  ATT  TTG  G  GA  TCC  CCA  AAT  TCT  CTT
```

1 2 3 4 | 5 6 7 8

− export      + export

```
0                                          BalI                                50
                                             |
YGSEGADLLD  GGEGNDLLKG  GYGNDIYRYL  SGYGHHIIDD  EGGKDDKLSL
    ▭                        ▭          ▭
------------------------------------------------------------
51                          BalI       DraI                                   100
                              |         |
ADIDFRDVAF  KREGNDLIMY  KAEGNVLSIG  HKNGITFKNW  FEKESDDLSN
    ▭          ▬▬▬                   ▬▬▬▬▬
------------------------------------------------------------
101                                                                           150

HQIEQIFDKD  GRVITPDSLK  KAFEYQQSNN  KVSYVYGHDA  STYGSQDNLN
   ▭             ▬▬▬
------------------------------------------------------------
151                       BglII                                               200
                            |
PLINEISKII  SAAGNFDVKE  ERSAASLLQL  SGNASDFSYG  RNSITLTASA
    ▭          ▬▬▬▬▬▬▬▬▬▬▬▬▬▬
------------------------------------------------------------
```

Fig.12

3 READING FRAMES OF E.COLI HAEMOLYSIN 23KD SECRETION SIGNAL
AVAILABLE FROM PROCHYMOSIN (PMG168) SMA1 SITE

```
                          SMA1
PPH - 1      CAG  GAG  CCC | GGG  GAA  AAT

SMA1
PPH - 2      CAG  GAG  CCC | GG  GAA  AAT

SMA1
PPH - 3      CAG  GAG  CCC | G  GGA  AAT
```

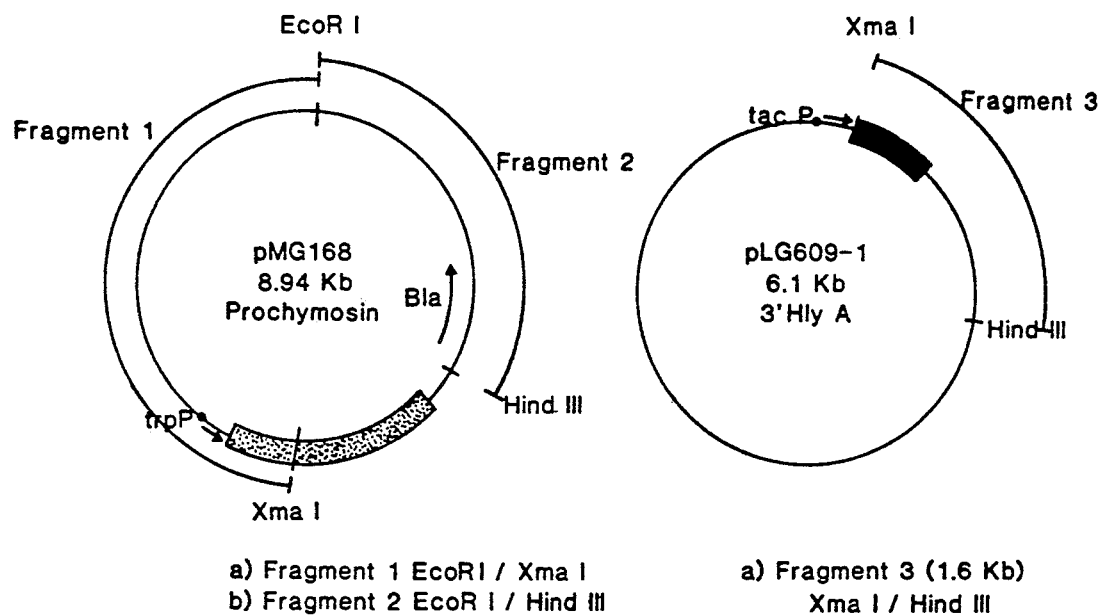
a) Fragment 1 EcoR I / Xma I
b) Fragment 2 EcoR I / Hind III
a) Fragment 3 (1.6 Kb) Xma I / Hind III
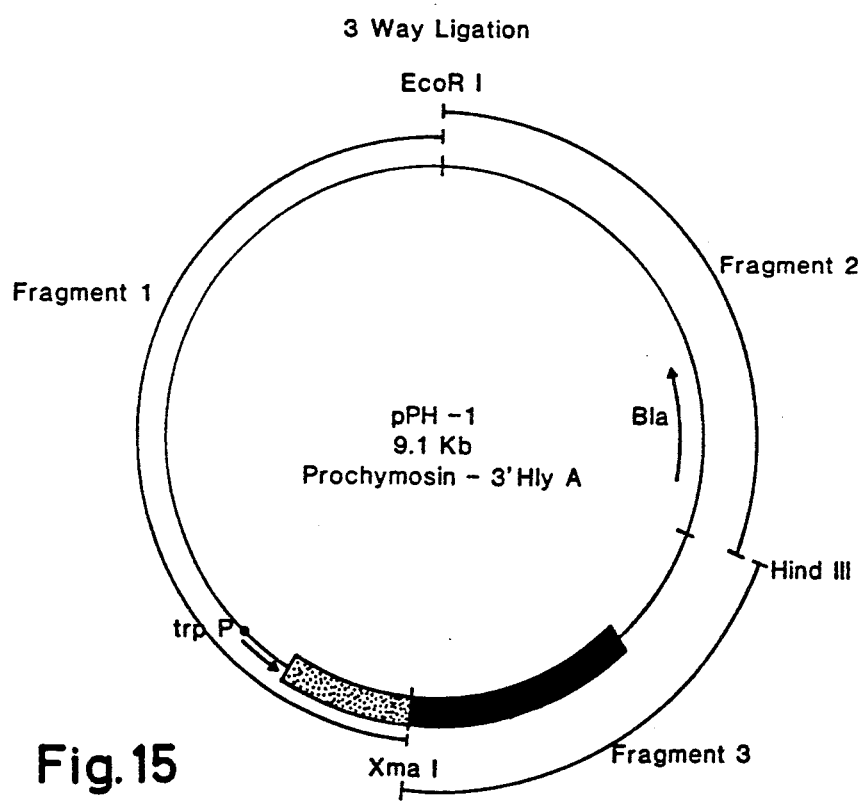
Fig. 15

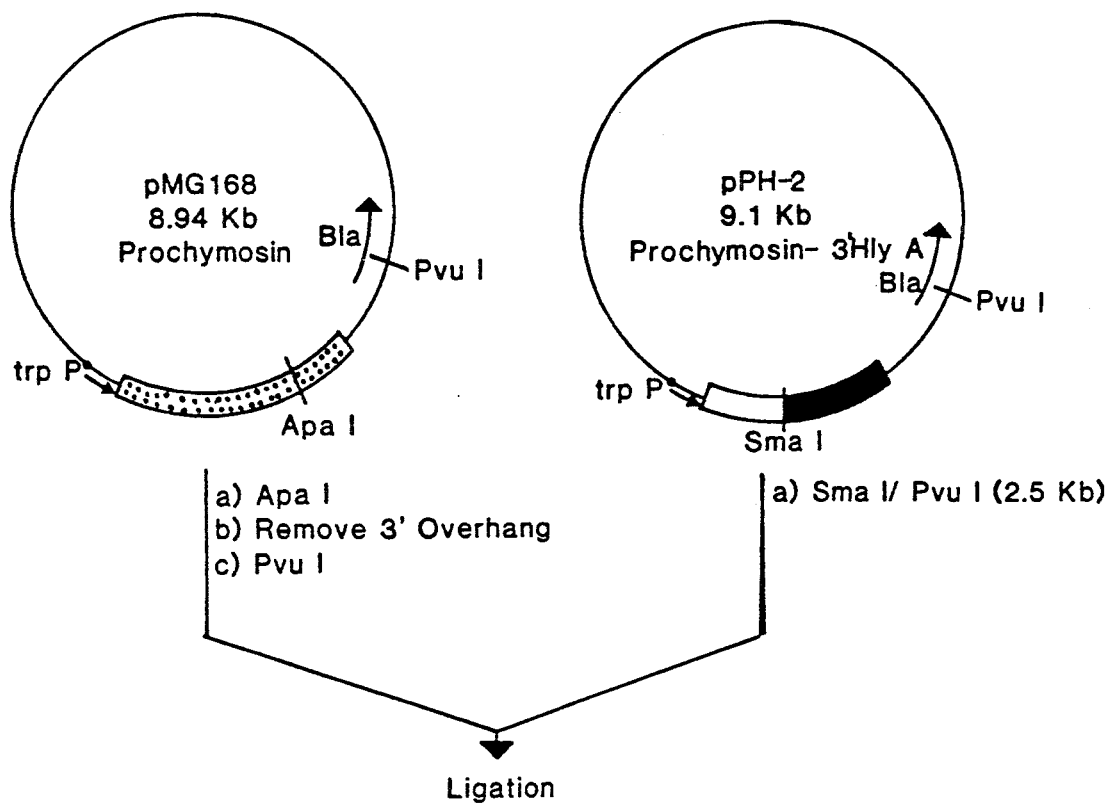
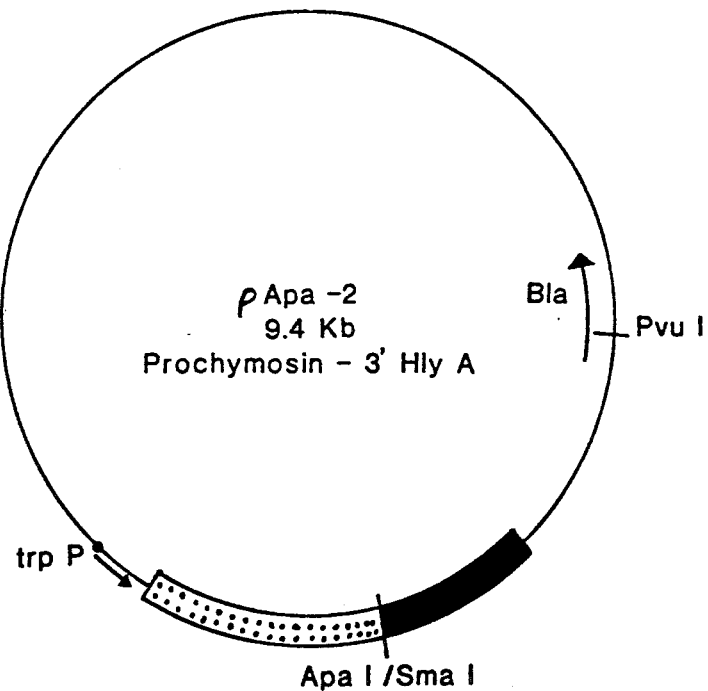
Fig.18

PROCESS FOR THE PRODUCTION OF A POLYPEPTIDE

FIELD OF THE INVENTION

This invention relates to recombinant DNA biotechnology and in particular to processes for the production of polypeptide products in transformed host cells wherein the polypeptide products are secreted from the host cells.

BACKGROUND TO THE INVENTION

In recent years advances in recombinant DNA biotechnology have made it possible to produce a wide variety of useful polypeptide products in host cells which have been transformed and transfected with DNA sequences which code for production of the polypeptide products. Thus hormones such as insulin and growth hormones e.g. human growth hormone, and industrially or therapeutically useful enzymes, such as chymosin and tissue plasminogen activator (tPA) have been produced in transformed host cells.

Bacterial cells, in particular *E. coli*, have been used as host cells for the production of recombinant polypeptide products. The genetic systems of such bacterial cells are now relatively well understood and also such cells exhibit good growth characteristics. However, when such bacterial cells are used to overproduce foreign proteins, the foreign products typically accumulate within the host cells and it is usually necessary to disrupt the cells to effect recovery of the products. Also recombinant products are often produced within bacterial host cells in the form of insoluble aggregates in which the polypeptides are not in their native, biologically functional form. It is necessary, therefore, to solubilise and denature/renature the insoluble polypeptide products to obtain useful products in soluble, native, biologically functional form. For instance, British Patent No. GB 2100732B describes inter alia processes for production of methionine-prochymosin in *E. coli* involving disruption of the bacterial host cells and treatment with urea or guanidine HCl to solubilise the unnatural prochymosin-containing aggregates which are produced. The processes of cell disruption and denaturation/renaturation add significantly to the cost of producing recombinant polypeptide products.

Attempts have been made therefore to develop bacterial expression systems which secrete recombinant products into the extracellular culture medium. For example, recombinant heterologous polypeptides have been expressed in bacteria as fusion proteins in which the heterologous polypeptide sequence is joined with an N-terminal signal sequence. However, such fusion proteins, although exported across the inner membrane in Gram-negative bacteria with concomitant removal of the signal sequence, fail to cross the outer membrane and remain within the periplasm. Thus, it is still necessary to disrupt the host cells to effect recovery of heterologous recombinant products and denaturation/renaturation treatment may be required to yield products in native, biologically functional form.

Also 'leaky' mutants of Gram-negative bacterial host cells such as *E. coli* have been proposed for use in the production and secretion of products to the extracellular medium. However, such mutant cells are often not suitable for large scale production of heterologous protein products since the yield of product is generally low and the fragility of the cells makes them unsuitable for growing on a large scale.

Haemolysin (Hly) is an extracellular protein toxin which is produced by some strains of *E. coli*, and as such is one of the few proteins produced by Gram-negative bacteria which are transported across both the cytoplasmic and outer membranes. Hitherto, however, the processes by which haemolysin is secreted to the extracellular medium have not been satisfactorily explained. Studies have indicated that a specific transport system determined by two of the hly genes is responsible for transport of haemolysin across the outer membrane (Wagner et al, J. Bacteriol. 154, 200, 1983), and at least four genes the hly A, hly B, hly C and hly D genes, are required to elicit a cell-free haemolytic phenotype. The hly C gene product appears to be required for activation of the hly A gene product which provides the haemolytically active species; whereas the hly B and hly D gene products (previously referred to as hly Ba and hly Bb) are essential for transport of haemolytic activity to the extracellular medium.

The primary product of the hly A gene does not contain an N-terminal signal signal sequence (Felmlee et al (1985) J. Bacteriol 163 p88–93). Thus, in an attempt to explain how secretion of the hly A gene product is achieved, Goebel and co-workers (Hartlein, M. et al, J. Cell Biochem. 22, 87–97, (1983)) have produced a model, in which the product of the hly A gene (107 Kd) is activated by the hly C gene product itself and is processed, possibly by an autoproteolytic activity located near the C-terminal end of the Hly A protein, to yield a smaller (58 Kd) haemolytically active peptide which is transported through the cytoplasmic membrane to the periplasm. They further propose that transfer of the 58 Kd haemolytically active peptide to the outer membrane and its release therefrom to the extracellular medium is promoted by the products of the hly B gene (46 Kd) and the hly D gene (62 Kd) respectively. Hartlein et al have also proposed the generation (by a proteolytic cut) of an N-terminal end of the 58 Kd fragment which can act as a signal peptide permitting transport of the fragment across the cytoplasmic membrane in the usual manner.

However, this explanation of the mechanism of secretion of the hly A gene product is controversial. Recently work in our laboratory and elsewhere has demonstrated the presence of large haemolytically active peptides, corresponding to the size of the initial hly A gene product, (107 Kd) in supernatants from cultures of haemolytic *E. coli*. This work suggests that cleavage of the Hly A protein is not required for production of the active extracellular haemolysin.

Hitherto, however, a satisfactory explanation of the mechanism by which haemolysin is secreted into the extracellular medium has not been forthcoming.

We have further studied the haemolysin secretion system and have shown that secretion of haemolysin from *E. coli* can be blocked by deletion of 27 amino acids from the C-terminus of the Hly A protein although this truncated molecule may be haemolytically activated by the hly C gene product. Further we have shown that a 23 Kd peptide from the C-terminus of Hly A contains all the information necessary for its own secretion. We have concluded, therefore, that all the information necessary for recognition and export of haemolysin in the presence of the hly B and hly D gene products, which appear to locate in the cell envelope, is contained within the 23 kilodalton C-terminal fragment of the hly A gene product. Our work constitutes the first finding of a C-terminal secretion sequence. Such C-terminal secretion sequences may be used in the preparation of recombinant fusion proteins which may be expressed and secreted from host cells.

The Hly B protein shows extensive homology (170 identical or conserved amino acid substitutions out of a stretch of 228 amino acids in the C-terminal region (Gerlach et al Nature 324 485–489 (1986)) with the p-glycoprotein Mdr (Multi-drug resistant protein) found in the surface of many drug resistant mammalian tumour cells. The Mdr protein is directly responsible for drug resistance and appears to function as an export pump (Ames, Cell 47 323–324 (1986)). The p-glycoprotein and haemolysin systems may therefore belong to a family of novel surface export mechanisms distinct from other export processes.

SUMMARY OF THE INVENTION

Accordingly, in a first aspect the present invention provides a process for the production of a polypeptide, in which host cells transformed with DNA coding for a fusion protein comprising the polypeptide and a further peptide comprising a C-terminal secretion sequence are cultured to express and secrete the fusion protein therefrom.

In the context of the present description 'a C-terminal secretion sequence' denotes a sequence of amino acids present in the C-terminus of a secreted polypeptide which sequence comprises essential information required for recognition and secretion of the secreted polypeptide via its secretion pathway. Preferably the C-terminal secretion sequence is a haemolysin C-terminal secretion sequence.

Thus in a preferred embodiment of the first aspect the invention provides a process for the production of a polypeptide in which host cells transformed with DNA coding for a fusion protein comprising the polypeptide and a further peptide comprising a haemolysin C-terminal secretion sequence are cultured to express and secrete the fusion protein therefrom.

The phrase 'haemolysin C-terminal secretion sequence' denotes a sequence of amino acids containing essential information required for recognition and export via the haemolysin secretion pathway. This sequence characteristically comprises at least part of a C-terminal sequence of an authentic *E. coli* haemolysin toxin or a substituted or modified equivalent thereof, provided it functions as a haemolysin C-terminal secretion sequence. Preferably the secretion sequence comprises a sequence identical to at least part of an authentic *E. coli* hly A gene product C-terminal sequence. The *E. coli* hly A gene product C-terminus may contain one or more sequences which function as C-terminal secretion sequences. For example, a secretion sequence may be identical to one or more subsequences of the 218 amino acid C-terminal sequence of Hly A as shown in FIG. 3. Without prejudice, we believe that at least one haemolysin C-terminal secretion sequence lies within the final 218 amino acid residues, especially within the final 150 amino acid residue, more especially within the final 113 amino acid residues and most especially within the final 32 amino acid residues of the Hly A C-terminus.

It will be appreciated, however, that provided the further peptide of the fusion protein contains a haemolysin C-terminal secretion sequence, it will function to promote secretion of the fusion protein. Therefore, the further peptide may contain further amino acids in addition to the secretion sequence. For example, additional amino acids may be required to separate the secretion sequence from the polypeptide in order advantageously to provide a favoured steric configuration in the fusion protein which promotes the secretion process.

Without prejudice to the generality of the present description, we believe that it may be advantageous to separate the secretion sequence from the polypeptide by up to 60 amino acids.

The process of the invention may be used for production of polypeptides in general, including natural and synthetic polypeptides and including polypeptides of bacterial origin. Preferably, however, the process may be used for production of heterologous polypeptides, i.e. polypeptides which are foreign to the host cells, especially eucaryotic polypeptides. For example, the polypeptides may be useful or therapeutic eucaryotic polypeptides such as hormones, enzymes and interleukins.

In a second aspect the invention provides a fusion protein comprising a first polypeptide and a further peptide in which the further peptide comprises a C-terminal secretion sequence, preferably a haemolysin C-terminal secretion sequence.

The fusion protein may comprise an internal fusion protein or an N-terminal fusion protein i.e. a fusion protein in which the further peptide containing the haemolysin C-terminal secretion sequence is joined to the N-terminal of the polypeptide. Preferably, however, the fusion protein is a C-terminal fusion protein, e.g. a fusion protein in which the further peptide containing the haemolysin C-terminal secretion sequence is joined to the C-terminus of the polypeptide. Typically, the fusion proteins comprise selective cleavage sites at the junction or junctions between the polypeptide amino acid sequence and the amino acid sequence of the further peptide. Such selective cleavaage sites may comprise one or more amino acid residues which provide a site susceptible to selective enzymatic, chemical or other cleavage. The fusion protein may be further processed to cleave the polypeptide therefrom; for instance, if the polypeptide is required without additional amino acid residues. Thus, the process of the first aspect of the invention includes a process in which, following secretion, the fusion protein is cleaved to yield the polypeptide.

In a third aspect the invention provides a DNA sequence coding for a fusion protein according to the second aspect of the invention.

The DNA sequence of the third aspect of the invention comprises a first DNA sequence coding for the polypeptide and a second DNA sequence coding for the further peptide and may include one or more additional DNA sequences which code for one or more selective cleavage sites at the junction or junctions between the first and second DNA sequences. The methods by which such DNA sequences may be obtained and linked to provide the DNA sequence of the third aspect of the invention are well known in the field of recombinant DNA technology. Thus DNA coding for the polypeptide may be obtained from parent cells which produce the polypeptide; for instance in the form of a cDNA sequence prepared by reverse transcription of mRNA obtained from the parent cells. Also DNA coding for the further peptide, containing a haemolysin C-terminal secretion sequence, may be obtained from the 3' terminal region of an hly A gene by appropriate restriction enzyme digestion.

Without prejudice to the generality of the present description, we believe that at least one haemolysin C-terminal secretion sequence may be present within the final 218, especially the final 150, and more especially the final 100 amino acid residues of the C-terminus of the Hly A protein. Thus the DNA coding for the further peptide may comprise a sequence present within the final 654, especially the final 450, more especially the final 339 and most especially the final 96 nucleotide residues of the 3' terminus of an hly A coding sequence. For example, this DNA may comprise a sequence present within the 654 nucleotides shown in FIG. 3, preferably within the final 450, especially within the final 339, and most especially within the final 96 of the 3' terminus therof. It will be appreciated, however, that it is the amino acid sequence coded by this DNA sequence which is involved in secretion and thus, in view of the redundancy of the genetic code, other DNA sequences which code for the relevant amino acid sequence may also be used. Furthermore, it will be appreciated that substituted or modified analogues of authentic haemolysin C-terminal secretion sequences may be used, and thus the DNA sequence coding for the further peptide may include any DNA sequence which codes for such analogue amino acid sequences. Usually, such analogues will have at least 80%, preferably at least 90%, most preferably at least 95% homology with the corresponding authentic haemolysin C-terminal secretion sequence.

Further, requisite DNA sequences may be wholly or partly synthesised by oligonucleotide synthesis techniques and sequences ligated using methods well known in the art.

Preferably the DNA sequence of the third aspect of the invention comprises a first 5' DNA sequence coding for the polypeptide and a second 3' DNA sequence coding for the further peptide, and especially also an additional DNA sequence coding for a selective cleavage site linking the 3' end of the first DNA sequence and the 5' end of the second DNA sequence.

The DNA sequence of the third aspect of the invention may be used in the construction of vectors, especially expression vectors, for transformation or transfection of appropriate host cells.

Thus, in a fourth aspect, the invention provides a vector comprising a DNA sequence according to the third aspect of the invention.

Such vectors typically include plasmids and are characteristically adapted for use in a given host cell type by the provision of selectable markers, promoters, optionally suitable replication sequences, and other control regions as appropriate. Such vectors include bacterial, e.g. *E. coli*, expression vectors such as plasmids derived from, for example, pBR322 and pAT153. Suitable selectable markers and promoters are well known in the art and include antibiotic resistance markers and promoters such as the tac promoter or the tryptophan operon promoters, e.g. the trpE promoter.

Vectors for transfection of mammalian cells may for example be based on bacterial plasmids such as pBR322 to which one or more suitable promoter/enhancers, selectable markers, promoters, eukaryotic replication origins and optionally polyadenylation sites have been added.

Furthermore, in a fifth aspect the invention also provides an expression vector containing a first DNA sequence coding for a peptide comprising a haemolysin C-terminal secretion sequence and an unique restriction site positioned relative thereto in such a way that expression of a fusion protein comprising the peptide and a further polypeptide may be obtained when a second DNA sequence coding for the polypeptide is inserted at the unique restriction site.

Preferably separate vectors according to the fifth aspect of the invention are provided to accommodate the second DNA sequence in any of the three reading frames relative to the reading frame of the first DNA sequence. Three such vector constructions are described hereinafter by way of example. Using such vectors DNA coding for a desired polypeptide may be inserted at the unique restriction site to provide an expression vector according to the fourth aspect of the invention. Vectors according to the fourth aspect of the invention may be used to transform or transfect appropriate host cells and the transformed host cells may be cultured to express fusion proteins according to the second aspect of the invention.

Thus in a sixth aspect the invention further provides host cells transformed with a vector according to the fourth aspect of the invention.

Suitable host cells include eukaryotic host cells e.g. yeast and mammalian cells and prokaryotic host cells which are typically bacteria, preferably Gram-negative bacteria, such as *E. coli*. Suitable mammalian hosts include, for example, chinese hamster ovary cells and rodent myeloma cells. It will be appreciated, however, that in order for the haemolysin secretion pathway to operate to secrete the fusion protein, it is necessary that the host cells also express functional Hly B and D proteins. Preferably the functional Hly B and D proteins may be present in, or may be produced in, the host cells in increased amounts. These proteins may be supplied by the host cells themselves; for instance, Hly+ host cells, e.g. *E. coli* SE5000, (pLG 570) may be used. Alternatively, the Hly B and D proteins may be provided by co-transformation or co-transfection of the host cells with an appropriate vector or vectors containing hly B and hly D genes. Such co-transformed or co-transfected hly B and hly D may be present in the same vector as the DNA sequence coding for the fusion protein or may be co-transformed or co-transfected in one or more further vectors. When the host cells are co-transformed with hly B and hly D genes they are preferably Rec A⁻ host cells.

The methods used for transformation and transfection of host cells and cultivation of transformed and transfected host cells are well known in the rec DNA art. A fusion protein comprising the desired polypeptide, is secreted by the host cells and thus may be advantageously recovered from the culture medium without need for disruption of the host cells and preferably does not require denaturation/renaturation treatment to give the polypeptide product in soluble, native, biologically functional form. The fusion protein may be further processed as required; for instance, cleaved to yield the polypeptide product.

BRIEF DESCRIPTION OF THE DRAWINGS

The invention is further described by way of illustration only in the following non-limiting examples which refer to the accompanying diagrams in which.

A. Graph of growth vs time for *E. coli* SE5000 transformed with plasmid pLG609 alone ( ) and co-transformed with plasmid pLG575 ( ).

B. SDS-PAGE gels of: Panel B—total cell protein of *E. coli* SE5000 (pLG609) samples taken over a period of time, and Panel C—samples of the culture supernatant fractions from *E. coli* SE5000 (pLG609/pLG575) taken over a similar period of time. Ac identifies the 23 Kd Hly A - C-terminal peptide.

FIGS. 3A and B show:

A. Restriction map comparison of hly A between pSF4000 and pLG570.

B. 657 nucleotides of coding sequence (lower line) of the 3' terminal of an hly A gene (pLG570) and the corresponding predicted 218 amino acid sequence (upper line) of the C-terminal of the Hly A protein.

Figure 4:
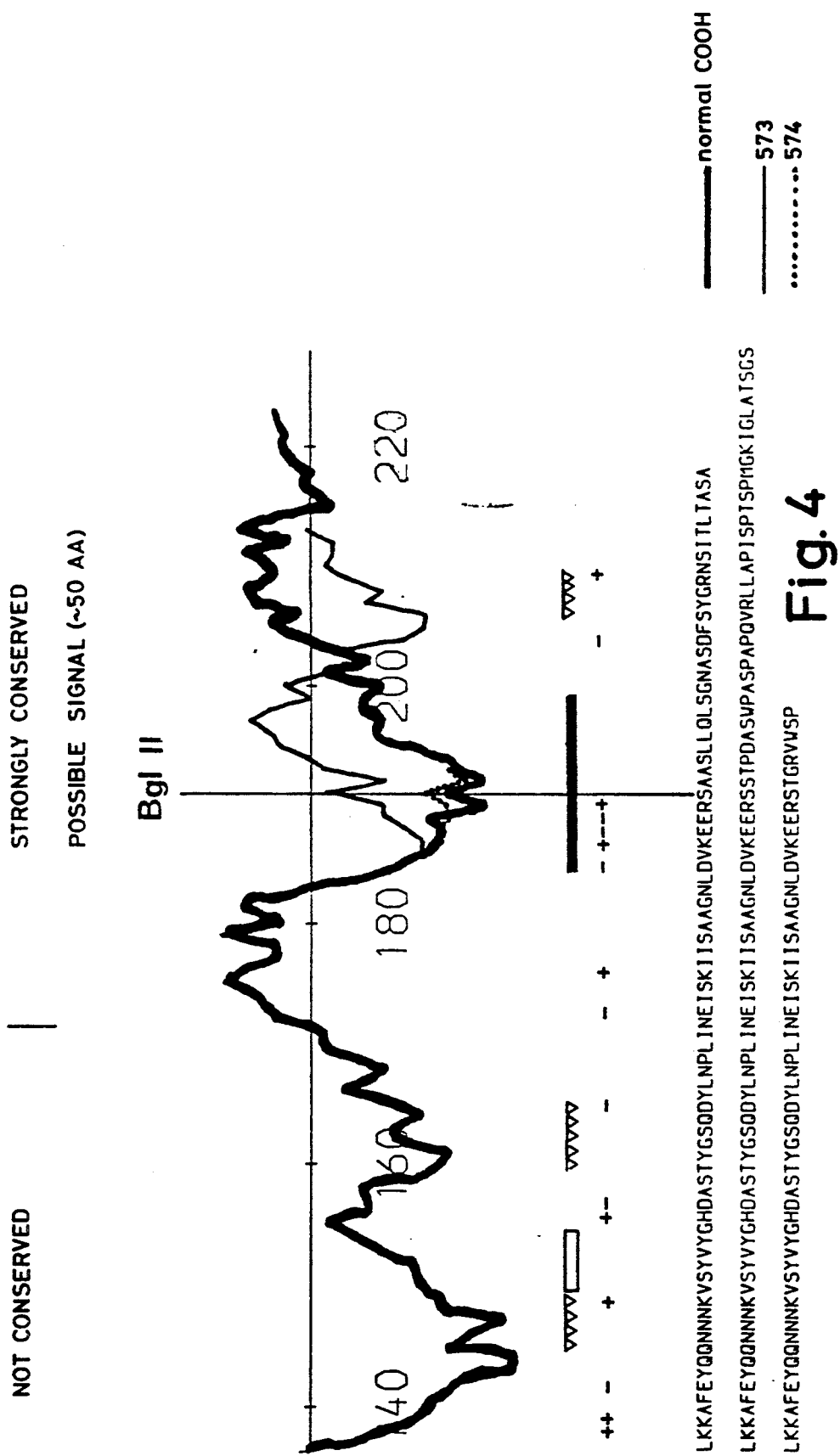

FIG. 4 shows: A graph of the hydropathic index of the final C-terminal 82 amino acids of the sequence of FIG. 3.

Figure 5A:
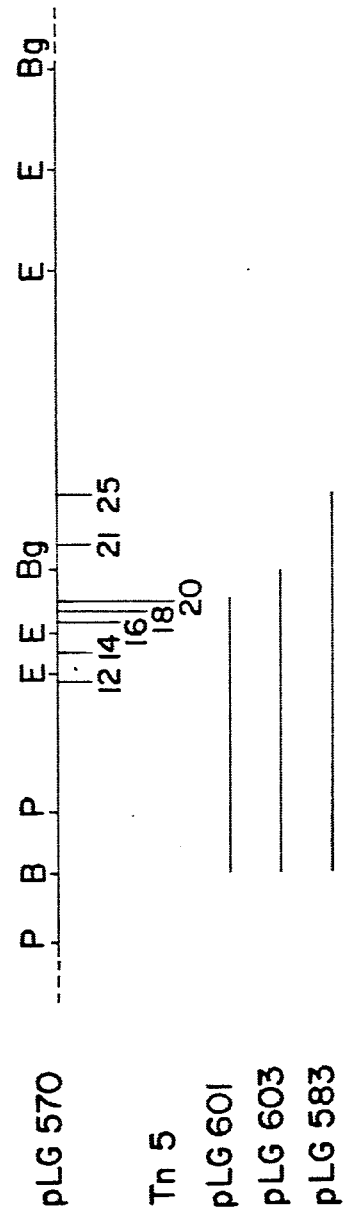

FIGS. 5A and B show:

A. Restriction map of the haemolytic determinant carried by pLG570, and position of Tn5 insertions.

B. SDS-PAGE analysis of total cell protein, obtained when pLG570:Tn 5-1 to 25 were complemented with pLG575 to provide export functions, followed by Western blotting and identification of gene products encoded by hly A with anti Hly A immune serum.

Figures 6, 7:
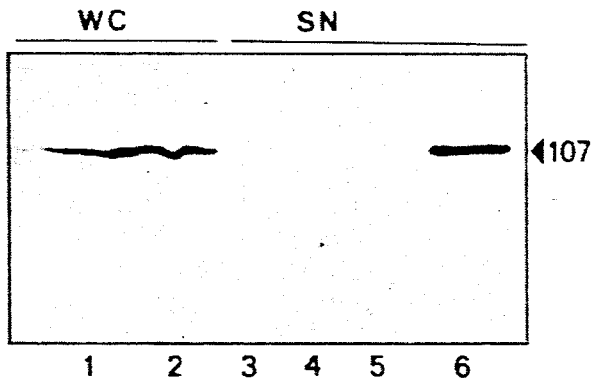

FIG. 6 shows: Analysis of proteins directed by pLG573 and pLG574.

FIG. 7 shows: The nucleotide sequence in the region of the inserted unique SmaI site of vector constructs pLG609-1, pLG609-2 and pLG609-3.

Figure 8:
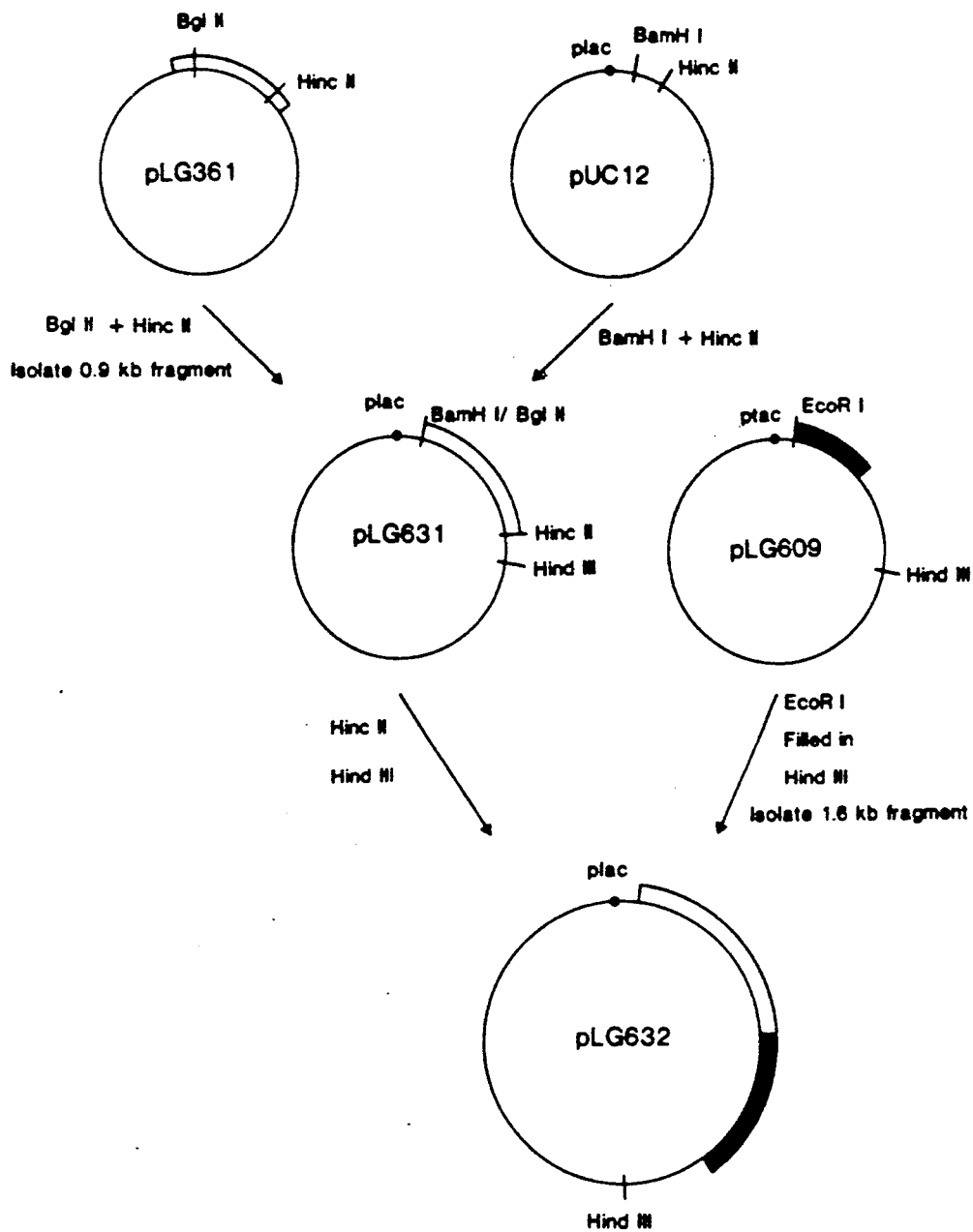

FIG. 8 shows: The construction of a lacZ-ompF-hly A gene fusion.

Figure 9A:
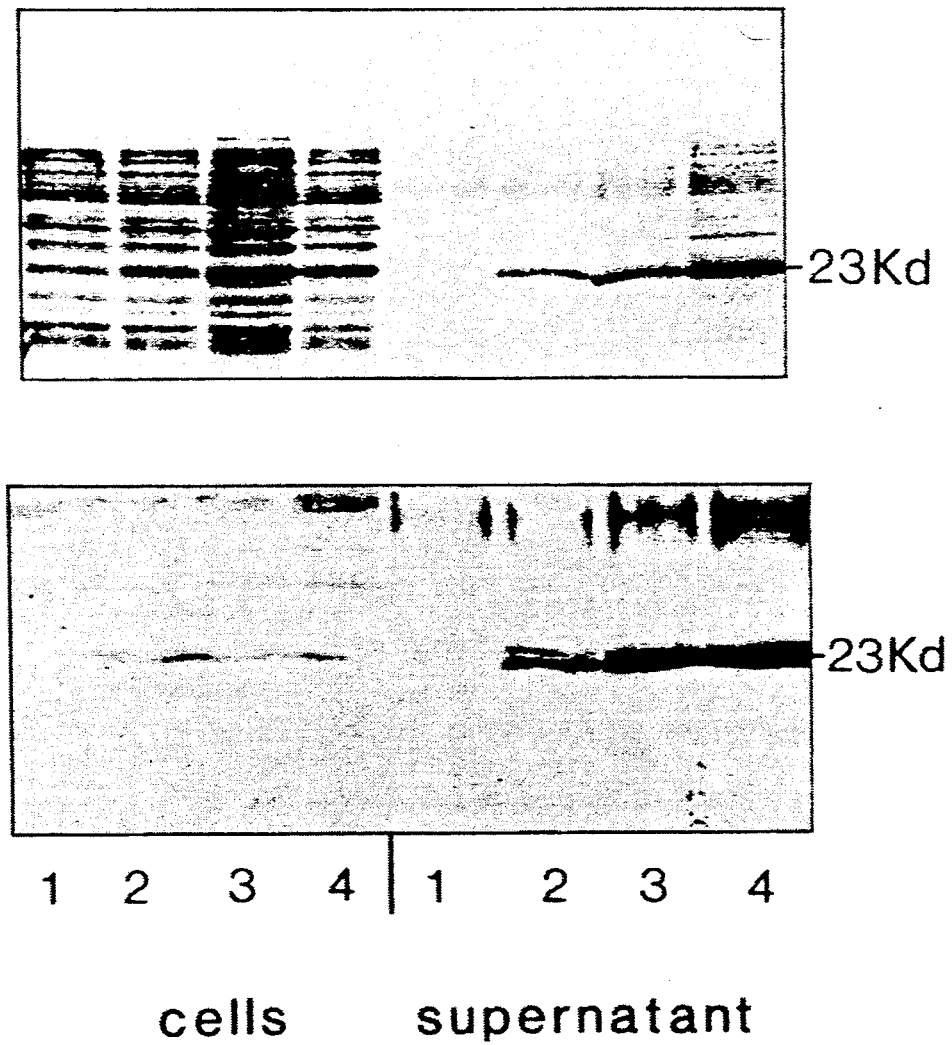
Figure 9B:
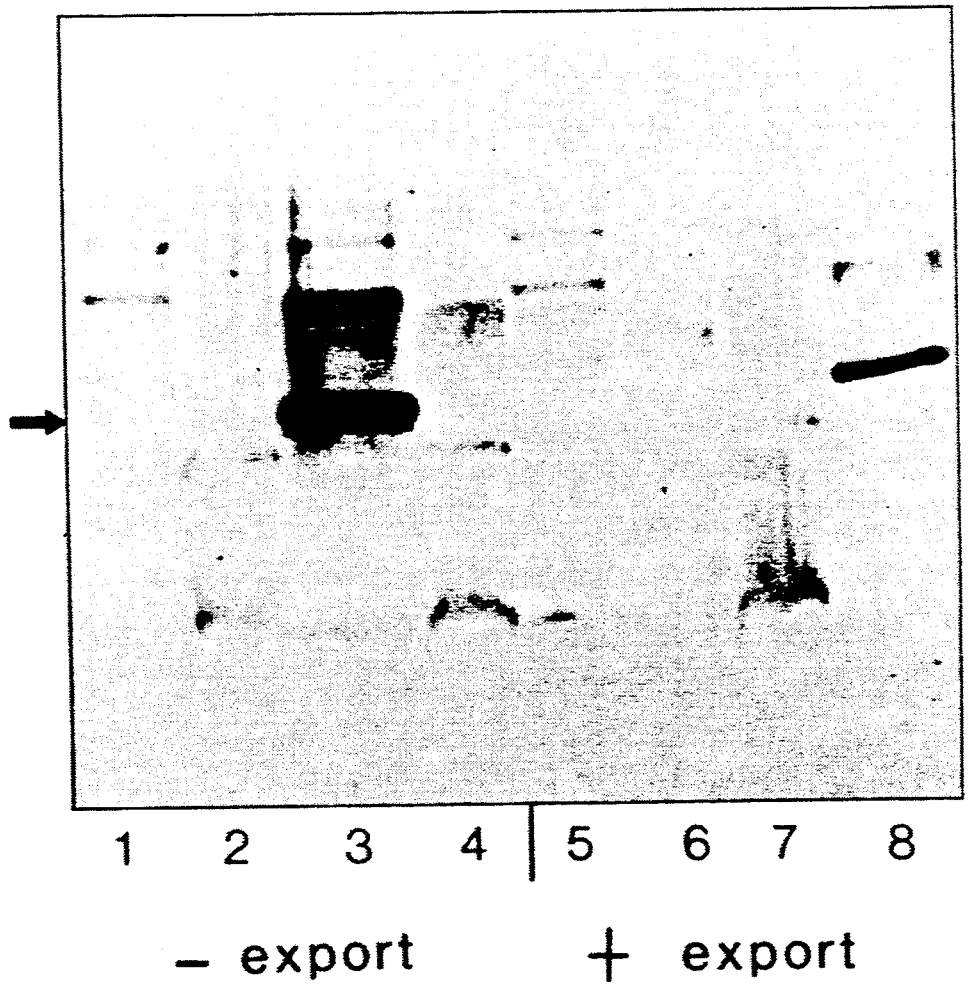
Figure 9C:
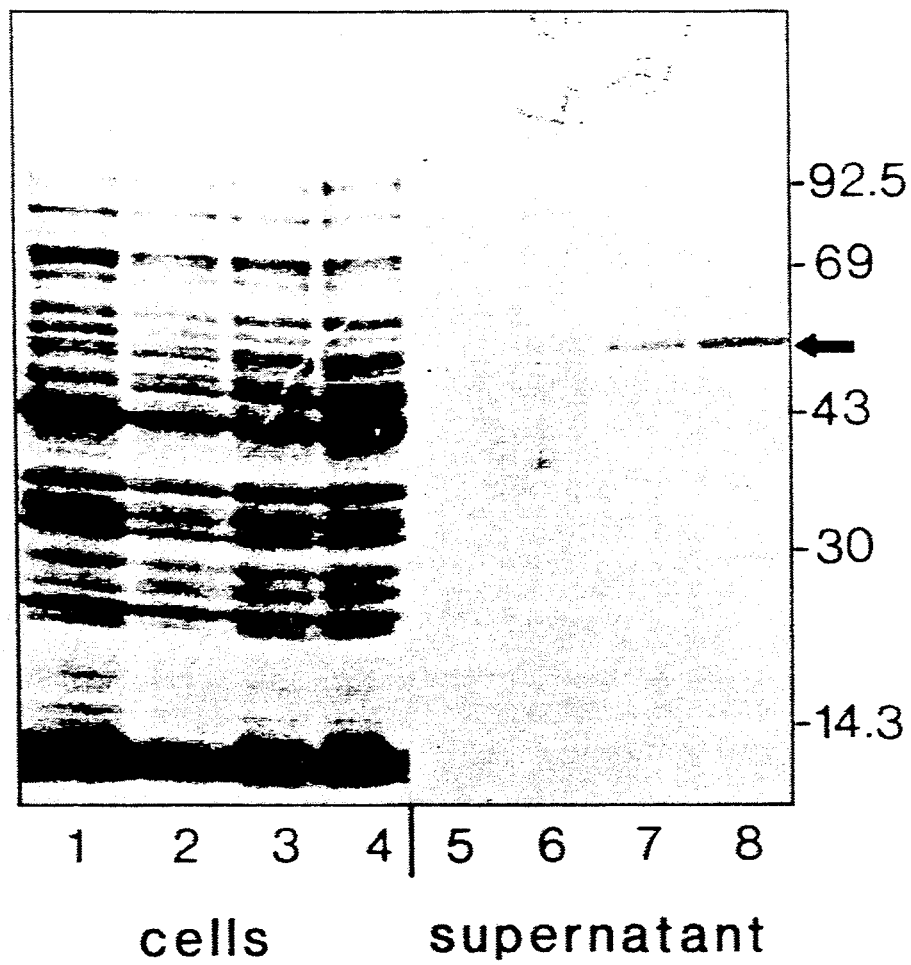

FIGS. 9A to C show:

A. SDS-PAGE analysis of the secretion of the 23 Kd C-terminal fragment of Hly A from *E. coli* SE5000 containing pLG609 encoding the 3' end of Hly A and pLG575 encoding Hly B and Hly D.

B. SDS-PAGE analysis of cell and culture supernatant samples taken from *E. coli* JM101 (pLG632/pLG575).

C. SDS-PAGE analysis of the time course of the secretion of the 56 Kd chimeric protein from *E. coli* JM101 (pLG632/pLG575).

Figure 10:
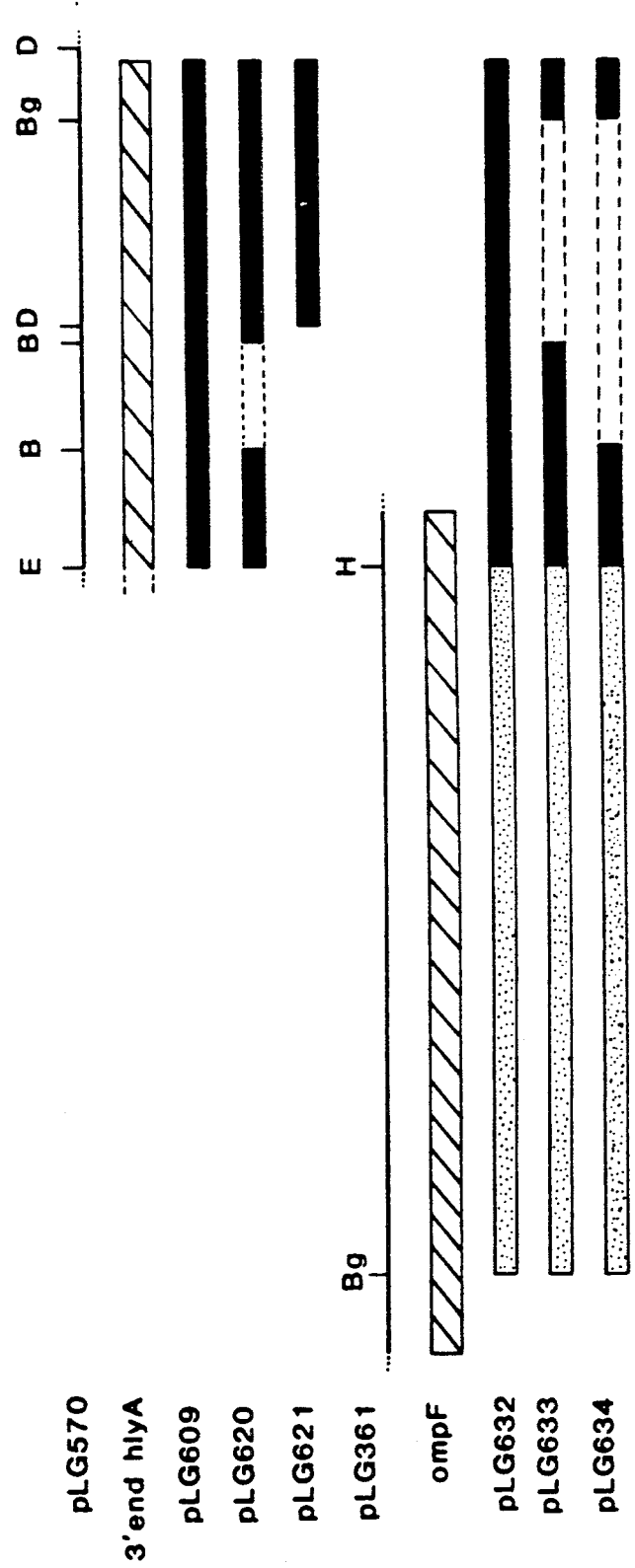

FIG. 10 shows: A partial map illustrating the construction of plasmids encoding various segments of the C-terminus of Hly A and deletion of hly A sequences from within the lacZ-ompF-hly A gene fusion.

Figure 11:
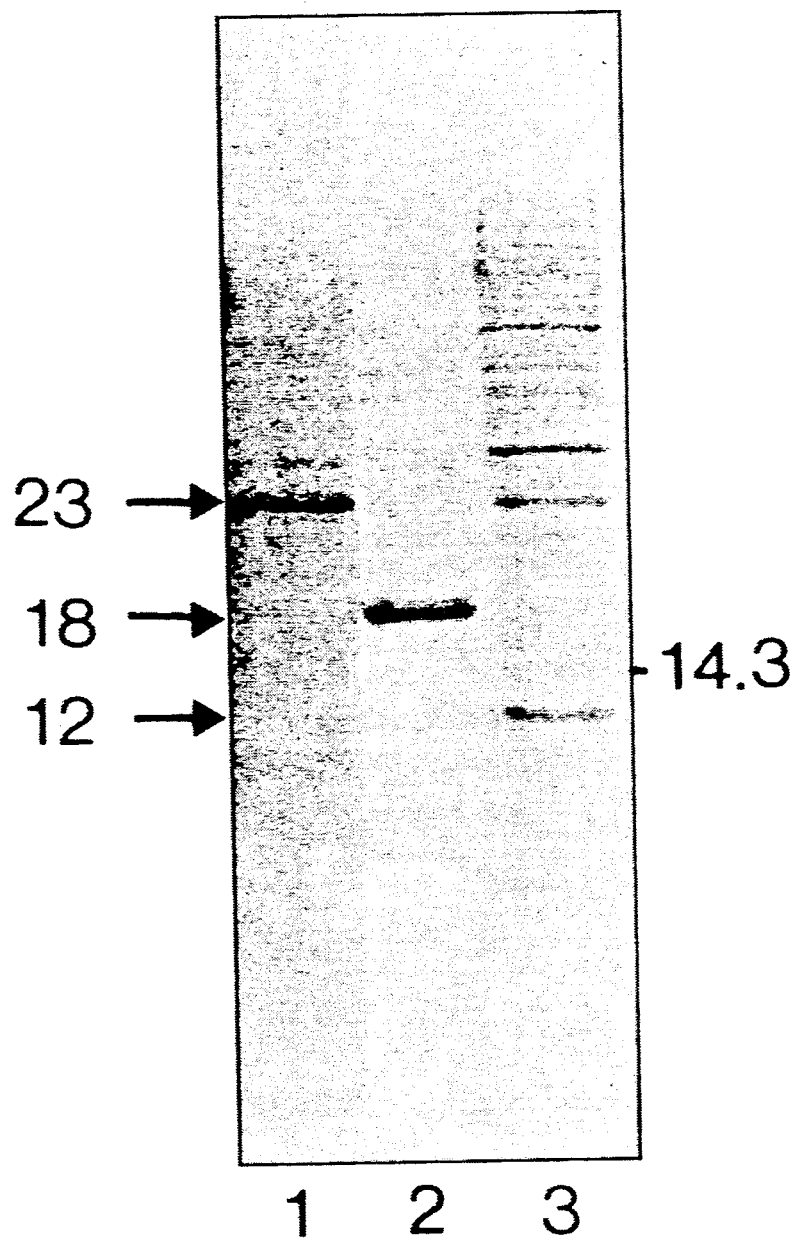

FIG. 11 shows: SDS-PAGE analysis of peptides secreted into the medium by *E. coli* JM101 (pLG575) carrying 1). pLG609; 2). pLG620; or 3). pLG621.

FIG. 12 shows: The sequence of the final 200 C-terminal amino acids of Hly A.

Figure 13:
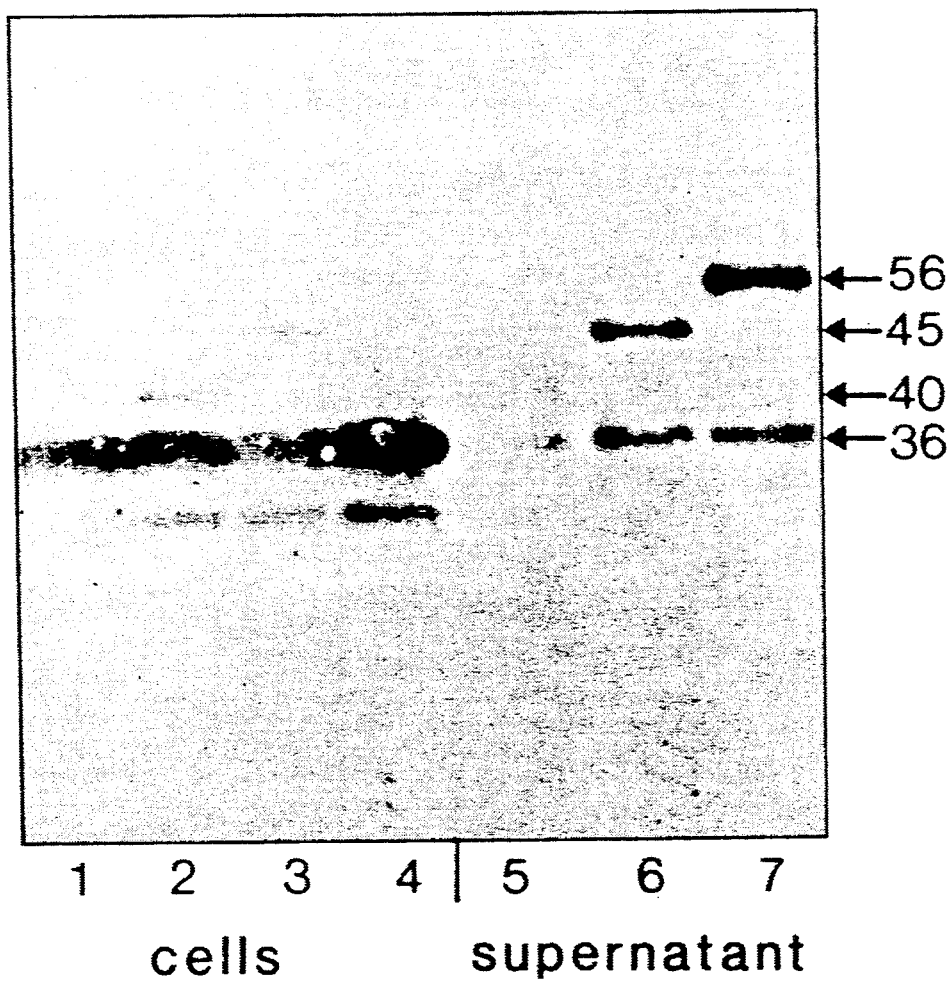

FIG. 13 shows: SDS-PAGE analysis of supernatant and cell samples of *E. coli* JM101 (pLG632/pLG575), *E. coli* JM101 (pLG633/pLG575) and *E. coli* JM101 (pLG634/pLG575).

Figures 14, 17:
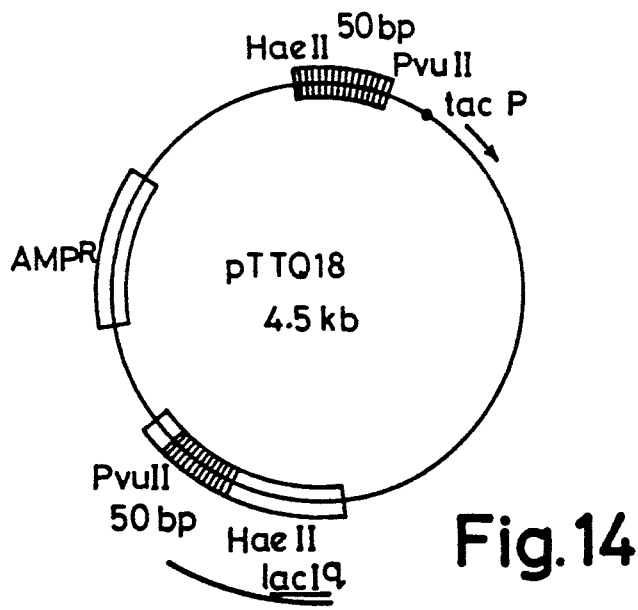

FIG. 14 shows: A map of plasmid pTTQ18.

FIG. 15 shows: Construction of plasmid pPH-1, carrying a fragment of the prochymosin gene with the hly A-C-terminal (23 Kd) coding region fused to the C-terminus.

Figure 16A:
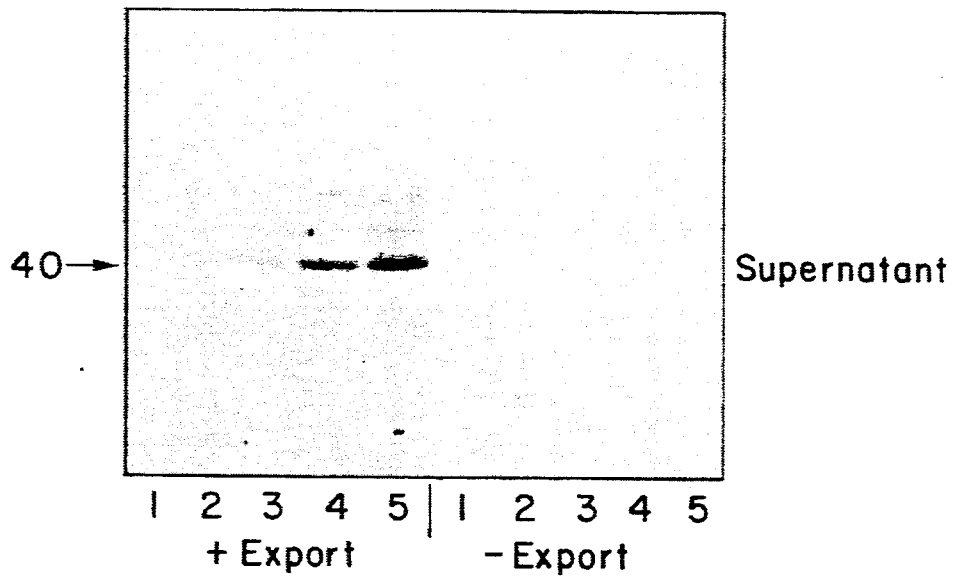

FIGS. 16A and B show: SDS-PAGE analysis of the production over a period of time of the 40K hybrid pro-chymosin-Hly encoded by pPH-1.

FIG. 17 shows: pPH-1, pPH-2 and pPH-3 which contain the *E. coli* haemolysin 23 Kd secretion signal available from the prochymosin (pMG168) SmaI site in each of the three reading frames.

Figure 19A:
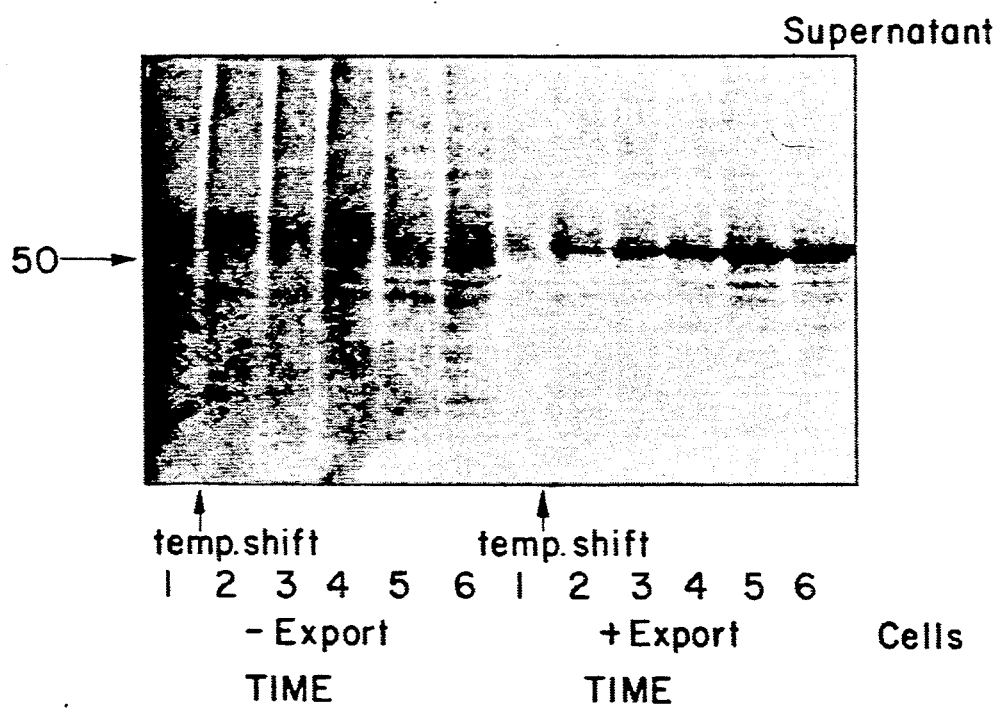

FIG. 18 shows: The construction of plasmid pApa-2,

FIGS. 19A and B shows: SDS-PAGE analysis of the production over a period of time of the 50K hybrid encoded by pApa-2.

DETAILED DESCRIPTION OF THE EMBODIMENTS

Materials and Methods

This section contains major methods used throughout the following examples. Other details to be found in references cited in text.

Bacterial Strains and Growth Conditions

*Escherichia coli* SE5000 rpsL, ara139, Δ(argF-lac) μ169, recA57; MC4100 rpsL, ara139, Δ(lac1POZA) μ169, thi; JM103 Δ(lac-pro), supE, thi, strA, endA, sbcB15, hsdR4; F'tra D36, proAB, lacIQ, ZΔ M15.

*Escherichia coli* JM101 supE, thi Δ(lac-proAB) (F', traD36, proAB, lacIq ZΔM15).

These strains were grown with aeration at 37° C. in L broth and for plasmid-containing strains chloramphenicol (25 μg/ml) or ampicillin (100 μg/ml) was added as appropriate.

Plasmids

Bacteriophage M13mp18 (Yanisch-Perron et al, 1985 Gene 33 103–119)

Vector plasmids pACYC184 cam$^R$, tet$^R$ (Chang and Cohen, 1978 J. Bacteriol. 134 1141–1156); pLG339, kan$^R$, tet$^R$ (Stoker et al, 1982); pUC12 amp$^R$, lacZ' (Norrander et al, 1983 Gene 26 101–106); pOU71 rep$^{ts}$, amp$^R$ (Larsen et al, 1984 Gene 28 45–54).

The relevant Hly markers carried by different plasmids are indicated in Table 1.

pLG570 contains a complete haemolysin determinant and purely for convenience has been deposited at and is freely available from the National Collections of Industrial and Marine Bacteria under Accession No. NCIB 12466. PLG570 has been deposited in an *E. coli* K12 SE5000 host. PLG575 is a subclone from pLG570 encoding the export genes, hly B and hly D (Mackman et al, (1985a) Mol. Gen. Genet. 201 282–288). pLG609 was constructed by inserting the 3' end of hly A behind the tac promoter of the expression vector pTTQ18 (Nicaud et al, (1986) FEBS. Lett. 204 331–335). pLG361 contains the ompF gene (Jackson et al, (1985) EMBO. J. 4 2377–2383). All the following plasmids pLG620, pLG621, pLG631, pLG632, pLG633 and pLG634 were constructed during these studies and are shown in FIGS. 8 and 10. Plasmid pLG603 was consructed as described in Gray et al (1986) (MGG 205 127–133) using plasmid pLG339 (Stoker et al (1982) Gene 18 335–341).

Preparation of Cell and Culture Supernatant Samples

Cultures were grown in rich medium to $A_{450}=0.4$ before IPTG (Sigma) was added to a final concentration of 50 μg/ml to derepress the tac or lac promoters. Cell samples were prepared by harvesting the cells and resuspending directly in SDS-sample buffer (Laemmli, (1970) Nature 227 680–685). Culture supernatant samples were prepared by first removing the cells by centrifugation (Sorvall SS34, 1600 rpm 15 min) and then adding TCA to a final concentration of 10% to the supernatant. Precipitated proteins were harvested by centrifugation (Sorvall HB4, 10000 rpm 10 min) and the TCA neutralised using a saturated Tris solution before proteins were solubilised in SDS-sample buffer.

Enzymes

Restriction enzymes and S1 nuclease were obtained from Bethesda Research Laboratories, T4 ligase from Biolabs and Klenow from Boehringer. Reaction conditions were those described by the manufacturers.

DNA Fragment Purification

DNA restriction endonuclease fragments were purified from agarose gels as described by Dretzen et al, (1981) (Biochem 112 295–298).

SDS-Polyacrylamide Gel Electrophoresis (SDS-PAGE)

The basic procedure was that of Laemmli (1970) (Nature 227 680–685) using either an 18% or 11% w/v acrylamide resolving gel with a 7% stacking gel; acrylamide monomer: dimer ratio of 44:0.8. Gels were stained using Coomassie brilliant blue (0.05% w/v) in a solution containing 10% v/v glacial acetic acid and 25% v/v propan-2-ol.

Western Blotting

Electrophoretic transfer of proteins from acrylamide gels onto nitrocellulose and subsequent immunological detection of proteins using either rabbit anti-Hly A or rabbit anti-OmpF and horseradish peroxidase conjugated to goat anti-rabbit IgG (Nordic Immunological) was carried out as described by Towbin et al, (1979) (Proc. Natl. Acad. Sci. USA 76 4350–4354) except that the substrate, o-dianisidine, was replaced by 0.5 mg/ml 3, 4, 3', 4'-tetra-aminobiphenyl hydrochloride.

Haemolytic Assay

Values for haemolytic activity can vary widely according to the particular Hly determinant, growth media (affecting stability), the host strain and cellular location. Spurious results can also arise through non-specific lysis of red cells (see below). In addition, release of haemoglobin is not an enzymatic process since the pore forming haemolysin is consumed in the reaction (Bhakdi et al 1986 Infect. and Immun. 52 63–69). For these reasons great care is required in establishing conditions in which haemolytic activity is directly proportional to the level of toxin present in different samples. Thus, fresh sheep erythrocytes (Oxoid) were always added in excess for each haemolysin sample i.e. conditions where the reaction (release of haemoglobin) followed linear kinetics over a selected time period. These optimal conditions were established by carrying out a preliminary time course experiment with a range of sample volumes. Individual bio-assays were then conducted as follows: duplicate sample vol. (5–50 $\mu$l) were mixed with washed erythrocytes in buffer (Mackman and Holland, 1984a MGG 193 312–315) to a concentration of 10% v/v erythrocytes in a final volume of 1 ml. These were incubated for 10 or 20 min respectively and then the remaining intact erythrocytes removed immediately by centrifugation. 700 $\mu$l of the supernatants from each sample were taken for measurement of free haemoglobin at $A_{543}$ in a spectrophotometer. The results for the 10 and 20 min incubations were used to confirm the linearity of the bio-assay and the average value taken.

1 unit of haemolytic activity was defined as the amount of toxin required to release 50 mg haemoglobin in 1 h per 1 ml of sample at 37° C. In the case of periplasmic samples, in which activity is usually extremely low or undetectable, the presence of 5 mM $MgCl_2$ in the buffer can cause spurious lysis of erythrocytes following centrifugation of the cells prior to measuring haemoglobin in the supernatant. This was avoided by removing the pelleted cells immediately from the supernatant fraction. In general, in order to minimise variation in haemolytic activities these studies where possible involved isogenic strain backgrounds and the samples for analysis were obtained from exponentially growing cells ($A^{450}=0.9$) in nutrient broth (Oxoid) plus 10 mM $CaCl_2$. Under these conditions haemolytic values in the medium are approaching the maximum (Nicaud et al, 1985a MGG 199 111–116). Finally, we observed that as cells approach the stationary phase the distribution of haemolysin changes leading to a slightly greater intracellular accumulation, although periplasmic values are still very low.

Detection of Hly A and Hly A Truncates with Antibody

As described by Towbin et al (1979 J. loc cit) proteins were separated by SDS-PAGE and then transferred to nitrocellulose by Western blotting. The Hly A derivatives were immunologically detected using anti-haemolysin antibody (Mackman et al 1985a MGG 201 282–288) followed by treatment with peroxidase-conjugated antibody.

Cell Fractionation

Cells were grown in nutrient broth supplemented with 10 mM $CaCl_2$. Periplasmic fractions were released by osmotic shock as described by Nossal and Heppel (1966 J. Biol. Chem. 241 3055–3062); sonication of the spheroplasts then led to the release of the cytoplasmic fraction. The relative contamination of fractions was monitored by assaying a whole cell sample and all individual cell fractions and washes for both malate dehydrogenase (MDH-cytoplasm) and $\beta$-lactamase activities (BLA-periplasm). MDH was assayed by addition of oxaloacetic acid and NADH, and monitoring the reduction in concentration of NADH. BLA was assayed as described by O'Callaghan et al (1972 Antimicrobial Agents and Chemotherapy 1 283–288). Fractions were only taken for further analysis when the cross contamination was less than 10%. In all cases activity in the fractions was greater than 95% of the whole cell sample.

Attempts to remove membranes from the cytoplasmic fraction by centrifugation resulted in complete and irreversible loss of haemolytic activity from both fractions during the procedure. All cytoplasmic fractions indicated therefore still contain cell membranes.

DNA Sequence Analysis

Restriction fragments cloned into the bacteriophage M13 mp18 were used as template for the dideoxy chain termination technique first described by Sanger et al (1977 Proc. Natl. Acad. Sci. 74 5463–5467). The resulting DNA sequence was analysed for hydropathy values (Kyte and Doolittle 1982 J. Mol. Biol. 157 105–132) and for the predicted secondary structure by Garnier (Garnier et al 1978 J. Mol. Biol. 120 97–120) analysis using

EXAMPLE 1

The C-terminal 23 Kd Peptide of *E. coli* Hly 2001 Contains all the Information Necessary for its Secretion by the Hly Export Machinery The production of haemolysin by certain pathogenic strains of *E. coli* is encoded by an approximately 7.5 kilobase sequence present on plasmids or integrated into the chromosome (Welch et al (1981) Nature 294 665–667; Muller et al (1983) J. Bact. 153 846–851). The Hly determinant is composed of at least 4 genes: hly A, the structural gene for the toxin; hly C, required for post translational modification of Hly A but not for its secretion; hly B and hly D, essential for export of the toxin through the envelope and into the medium (Mackman et al (1985a) MGG 201 282–288; Nicaud et al (1985b) FEBS Lett. 187 339–344). Previous studies have demonstrated that hly A encodes a 107 kilodalton polypeptide (Nicaud et al (1985a) MGG 199 111–116; Gonzalez-Carrero et al (1985) MGG 99 106–110) which is exported to the medium without proteolytic processing of the N-terminus (Felmlee et al (1985a) J. Bact. 163 88–93).

Furthermore, DNA sequence data for hly A indicates the complete absence of an N-terminal signal sequence (Felmlee et al (1985b) J. Bact. 163 94–105). In view of this and the apparent absence of a periplasmic intermediate in haemolysin secretion, we have proposed a model for export of the haemolysin (Mackman et al (1986) Curr. Top. Micro Immun. 125, p159–181, Springer Verlag). In this we envisage a first step involving recognition of cytoplasmic Hly A by the export machinery located in the inner membrane followed by a second step which results in direct extrusion of the toxin to the medium.

Recently, we have shown that secretion of haemolysin from *E. coli* can be blocked by deletion of approximately 27 amino acids from the C-terminus of Hly A, although this truncated molecule is still haemolytically active. In this Example we describe additional evidence that a secretion signal is entirely located in the C-terminus of Hly A.

Construction of Plasmid pLG609 Encoding a C-Terminal Fragment of Hly A

This was achieved (see FIG. 1) by subcloning a 1.6 kilobase EcoRI-HindIII fragment encoding the 3'-end of hly A from pLG570 in the correct reading frame for subsequent translation into the high copy expression vector, pTTQ18. This plasmid carries a tac promoter upstream of a multicloning and expression-site, together with the lacIq gene in order to ensure that expression from the cloned gene is completely repressed in the absence of the inducer IPTG. Bagdasarian M.M. et al (Gene 26 273–282 (1983)) describe analogous vectors to pTTQ18 which may also be used to sub-clone the 3' end of hly A. The resulting recombinant plasmid, pLG609, should contain a hybrid gene with the tac promoter fused to the 3' end of hly A which should then direct the synthesis of a 23 kilodalton polypeptide (Ac) corresponding to the C-terminus of Hly A.

Growth of *E. Coli* SE5000 (pLG609) in the Presence and Absence of pLG575 (hly B, D)

The presence and orientation of the EcoRI-HindIII fragment in the plasmid vector was confirmed by restriction enzyme analysis.

Figure 2:
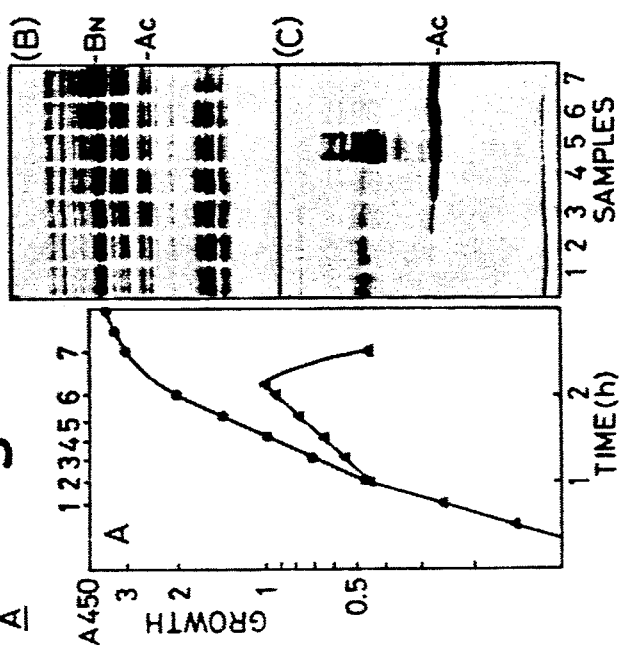
FIGS. 2A and B show.

The growth characteristics of strain SE5000 (pLG609) were studied in the presence or absence of pLG575 (Mackman et al (1985a) MGG 201 282–288) a plasmid carrying hly B and D, and with addition of IPTG in order to induce synthesis of Ac from the tac promoter. FIG. 2a shows that addition of IPTG to a strain carrying pLG609 with no hly export functions resulted in rapid cessation of growth. In contrast, when the export functions were also present the addition of IPTG had little effect on growth.

This result indicated that the intracellular accumulation of a polypeptide, most probably Ac, in the absence of Hly export proteins was toxic for the cell and that this effect could be alleviated by export of the Ac protein to the medium.

The 23 Kd C-Terminal Fragment of Hly A is Secreted

The protein content of the cells and medium from the experiment shown in FIG. 2a were analysed by SDS-PAGE. First, FIG. 2b shows the induction of the synthesis of small amounts of a 23 kilodalton polypeptide in the total cell lysate of strain SE5000 carrying only pLG609 whereas no 23 kilodalton protein was detected in the culture supernatant (data not shown). In contrast, however, as shown in FIG. 2c, in the presence of the export functions substantial quantities of a 23 Kd polypeptide accumulated in the medium after addition of IPTG. The identity of the 23 Kd protein as a fragment of Hly A was confirmed by the use of antiserum to purified haemolysin (Nicaud et al (1985b) FEBS Lett. 187 339–344) (data not shown). At least one other major polypeptide accumulated intracellularly following the addition of IPTG but this protein was produced by the vector alone, in the absence of the hly fragment (data not shown).

The results presented here demonstrated unequivocally that the C-terminal, 23000 dalton peptide of Hly A contains all the information necessary for its own secretion. As expected, secretion was only observed in the presence of the specific haemolysin export proteins, Hly B and Hly D, and does not require Hly C (Nicaud et al (1985b) FEBS Lett. 187 339–344). These results, taken together with the data in Example 2 (see also Gray et al 1986, MGG 205 127–133) that deletion of a small region at the C-terminus of Hly A blocks secretion, strongly suggests that a small region close to the C-terminus contains all the information necessary for secretion of the intact haemolysin. Our results are therefore consistent with a mechanism in which the C-terminal region of Hly A specifically interacts with Hly B and/or Hly D in order to facilitate secretion. Preliminary studies indicate that these latter proteins are located primarily within the inner membrane, although significant levels of Hly D also fractionate with the outer membrane (Mackman et al (1985b) MGG 201 529–536). In the absence of Hly B and D, the 107,000 dalton protein accumulates intracellularly (Gray et al MGG 205 127–133 (1986).

EXAMPLE 2

Deletion of the Hly A C-terminus blocks secretion but not haemolytic activity.

1. Intracellular Localisation of Normal Haemolysin in the Presence or Absence of Export Functions, hly B, hly D In this study we took advantage of the availability of various subclones of the Hly determinant 2001 (Table 1, Mackman et al 1985a MGG 201 282-288), including those carrying one or both export genes, to determine the effect of the presence of these genes in complementation tests on the production and localisation of any intracellular haemolysin. For the purpose of this analysis each gene was always supplied by the same vector. Thus the source of hly C was pUC12 (ca 60 copies); hly B, D, pACYC184 (ca 20 copies); hly A pLG339 (ca 6 copies). This ensured that the results were comparable and the Hly C, B D proteins were present in excess. The results of these analyses with that for the fully reconstituted system (e.g. pLG583 hly A, 577 hly C, 591 hly B, D) are indicated in Table 2.

Under conditions for secretion of Hly A to the medium a maximum of 2% of haemolytic activity was usually found within the cells of exponentially growing cultures. Moreover, virtually 100% of this low level activity was found within the cytoplasm with insignificant levels in the periplasm as detected by osmotic shock. When either export function was absent the total production of haemolysin was reduced five to ten-fold, suggesting some form of feedback regulation on the synthesis or degradation of intracellular haemolysin. Analysis of the haemolytic activity within different cellular compartments in the absence of either or both export functions during exponential growth revealed that more than 90% of the residual activity was always present in the cytoplasm (Table 2).

TABLE 1

| Plasmid | Resistance | Genes | Reference |
|---|---|---|---|
| pLG 570 | amp | complete hly determinant | Mackman and Holland (1984b) |
| pLG 579 | tet | hly B | Mackman et al (1985a) |
| pLG 575 | cam | hly B hly D | " |
| pLG 577 | tet | hly C hly A''' | " |
| pLG 573 | cam | hly A' | " |
| pLG 574 | cam | hly A'' | " |
| pLG 583 | kan | hly A | " |
| pLG 603 | kan | hly A' | Gray et al (1986) |
| pLG 594 | cam | hly D | Mackman et al (1985b) |
| pLG 591 | amp | hly C | Nicaud et al (1985b) | hly A' = hyl A/tet fusion resulting in 107 Kd polypeptide
hly A'' = hyl A/tet fusion resulting in 104 Kd polypeptide
hly A''' = hyl A truncate resulting from termination of the gene at the EcoRI site

TABLE 2

| | Cellular fractionation of haemolytic activity | | | |
|---|---|---|---|---|
| Plasmids | Hly functions | Medium | Periplasm | Cytoplasm |
| 1. None | None | <0.01 | <0.01 | <0.01 |
| 2. pLG591, 583, 575 | CABD | 15.4 | <0.01 | 0.3 |
| 3. pLG591, 583 | CA- | <0.01 | 0.2$^a$ | 2.4 |
| 4. pLG591, 583, 579 | CAB- | <0.01 | 0.1$^a$ | 1.5 |
| 5. pLG591, 583, 594 | CA-D | <0.01 | 0.1$^a$ | 1.5 |
| 6. pLG570:Tn5-2, 573, 579 | CA'BD* | 0.8 | 3.1$^b$ | |
| 7. pLG570:Tn5-2, 574, 579 | CA''BD | 0.2 | 2.5$^b$ | |
| 8. pLG577, 603, 575 | CA'BD | 0.84 | 0.01 | 1.37 |

*Symbols A', A'', as in Table 1.
$^a$in this case level of contamination of the periplasmic fraction with cytoplasmic malate dehydrogenase reached 10%.
$^b$intracellular activity.

2. Effect of Tn5 Insertions into hly A on Secretion of the 107 Kd Protein

Figure 5B:
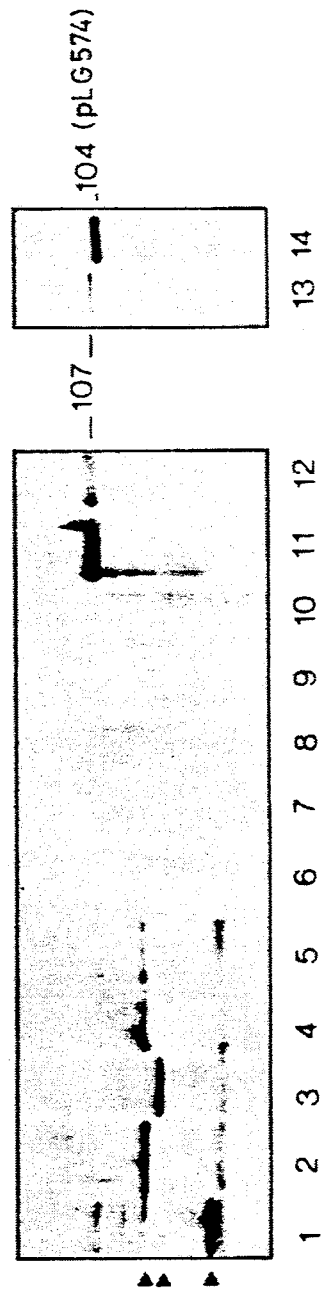

A family of deletions of the C-terminus of Hly A was isolated by insertional mutagenesis with Tn5 as described previously (Mackman and Holland, 1984b MGG 196 129-134). The position of the Tn5 insertions was mapped as shown in FIG. 5a. In all cases tested Tn5 insertion into hly A resulted in the absence of both extracellular and intracellular haemolytic activity (data not shown). However, when total cell proteins were analysed by SDS-PAGE followed by Western blotting and identification of gene products encoded by hly A with anti Hly A immune serum, truncated derivatives of Hly A were detected. In contrast, no cross reacting material was detected in the medium (FIG. 5b). The tracks of the gel shown in FIG. 5b are as follows:

Tracks 1-5 whole cell lysates; Track 1 Tn5-12; Track 2 Tn5-14; Track 3 Tn5-16; Track 4 Tn5-18; Track 5 Tn5-20; Tracks 6-12 Culture Supernatants; Track 6 Tn5-12; Track 7 Tn5-14; Track 8 Tn5-16; Track 9 Tn5-18; Track 10 Tn5-20; Track 11 Tn5-21; Track 12 Tn5-25; Tracks 13 and 14 products of in vitro transcription translation programmed by pLG573 and pLG574 respectively.

These results indicated that removal of a large portion of the C-terminus of Hly A always resulted not only in the loss of activity, but also in the ability of the remaining part of the molecule to be secreted.

The data in FIG. 5, also shows that several insertions close to the 3'-terminus of hly A resulted in truncated polypeptides all with a molecular weight of about 80 Kd. This suggested that such insertions result in the formation of abnormal polypeptides which are all proteolytically digested back to a protease resistant domain of about 80 Kd. In view of this phenomenon an alternative source of a specific C-terminal deletion of Hly A was sought.

3. Isolation of a Subclone Lacking the 3' end of hly A

Previously (Mackman et al 1985a MGG 201 282-288), we have described the construction of a plasmid, pLG574 carrying a 3 kb BamHI-BglII fragment which appeared to encode a slightly truncated form of Hly A in vitro. Thus, unlike the Hly A deletions described above, this plasmid encoded a polypeptide close to normal size which was nevertheless stable. We then examined the size of the truncated form of the toxin produced by pLG594. An additional subclone pLG573, carrying the 3Kb BamHI-BglII fragment in the opposite orientation (Mackman et al 1985a), was also included in the analysis.

As shown in FIG. 5b (track 14), pLG574 encodes the synthesis of an approximately 104 Kd polypetide in vitro. PLG573 directed the synthesis of a polypeptide apparently indistinguishable in mobility in SDS-PAGE from the Hly A protein (107 Kd) encoded by the intact determinant in pLG570. In fact, inspection of the downstream sequences within the tet gene (Peden, 1983 Gene 22 277–280) in either orientation predicts in frame fusions which would add 37 and 17 amino acids to the Hly A protein encoded by pLG573 and pLG574 respectively (see FIG. 4). This would result in the synthesis of proteins with molecular weights similar to those observed in FIG. 5. The alternative possibility that the original hly A sequence contains two closely linked BglII sites close to the 3' end was eliminated by sequencing this region of DNA (FIG. 3).

4. Properties of Hly A Proteins Encoded by pLG573 and pLG574

Exponentially growing cultures of strain MC4100 carrying pLG573 or pLG574 together with an additional plasmid pLG570:Tn5-2 and pLG579 providing hly C, D and hly B respectively in trans were analysed for the presence of haemolytic activity. Alternatively, plasmids pLG577 and pLG594 may be used as a source of hly C and hly D respectively. The results in Table 2 (line 6, 7) clearly demonstrated that strains carrying either pLG573 or pLG574 produced only low levels of extracellular activity. Moreover, in both cases there was now several fold more haemolytic activity inside the cells compared to that in the medium. Furthermore, on sheep blood plates, which we have found forms an extremely sensitive test for secretion, the presence of pLG574 in bacterial colonies failed to promote any detectable release of haemolysin whilst pLG573 gave only very small haloes (data not shown). These results strongly suggested that the truncated forms of Hly A produced from pLG573 and pLG574 were defective in secretion. In order to confirm this effect under conditions comparable to those described in the first section above, the BamHI-BglII fragment encoding hly A in pLG573 was transferred to the low copy number vector, pLG339, generating the recombinant plasmid, pLG603 (see FIG. 5a). Production of haemolytic activity directed by this plasmid was measured and once more we observed a greater than 10–20 fold reduction in the extracellular level of haemolysin (Table 2, line 8) compared to comparable constructions encoding the intact Hly A.

The levels and localisation of Hly A protein, directed by pLG573 and pLG574 in the presence of the export functions were also analysed by immunoblotting using antibody to Hly A.

FIG. 6 shows proteins separated by SDS-PAGE transferred by Western blotting to nitrocellulose and visualised using anti-haemolysin antibody followed by staining with perioxidase conjugated antibody. pLG573 and pLG574 were complemented with pLG579 and pLG570:Tn5-2 providing hly B and hly C, D respectively in trans. Tracks 1–2 whole cell lysates. Track 1 pLG574; Track 2 pLG573. Tracks 3–6 culture supernatants. Track 3 pLG574; Track 4 pLG573; Track 5 *E. coli* culture supernatant no plasmid; Track 6 authentic Hly A (107K) from pLG570.

As shown in FIG. 6 insignificant amounts of Hly A were detected in the medium with either pLG574 (track 3) or pLG573 (track 4). However, intracellular levels of 107 Kd polypeptide were readily detected in both cases (FIG. 6, track 1, 2).

5. DNA Sequence of the 3' End of hly A 2001

Since the C-terminal region of Hly A is clearly involved in the secretion process it was necessary to obtain the DNA sequence of the corresponding region of hly A. The results of the DNA sequence analysis and the predicted amino acid sequence for the last 218 residues compared with those of Hly psF4000 described by Felmlee et al 1985b (J. Bacteriol. 163 94–105), are presented in FIG. 3b.

The overall sequence in this region is highly conserved, with 95% homology at the DNA level, and 94% homology at the amino acid level. The sequence data and restriction enzyme analysis also confirmed the restriction enzyme site differences between Hly 2001 and the sequence of Felmlee et al. This included the surprising finding that the BglII site in the latter sequence has been replaced by a quite different BglII site (FIG. 3a). This BglII site in the Hly A 2001 sequence is extremly close to the terminus and enabled us to generate the 27 amino acid deletion of Hly A described above.

From the Hly A 2001 sequence data and knowledge of the down stream sequences at the cloning site junctions a profile of the hydropathy index for the terminal 82 amino acids of Hly A and for the deletions in pLG574 and pLG573 generated by cleavage at the BglII site was obtained (FIG. 4). In addition to the likely structure of the terminal regions formed in pLG573 and pLG574 the figure indicates the position of the BglII site which coincides with a rare feature in the predicted secondary structure of Hly A, a short α helical region. This feature is conserved in HlySF4000 as is a stretch of 13 relatively hydrophobic amino acids (residues 191–203) overlapping the predicted α helix between residues 185–196.

EXAMPLE 3

Subclones of pLG609 using EcoR1 Linker DNA to Generate Different Reading Frames in the Hly, 23 Kd Secretion Signal Region Plasmid pLG609, derived as described in Example 1, was digested with the restriction endonuclease EcoR1. Three synthetic oligonucleotides:

1). GAATTTTCCCCGGGGAA
2). GAATTTTCCCGGGAA
3). GAATTTCCCGGGA containing a SmaI recognition site were synthesised using methods well known in the art and ligated with the digested pLG609 to yield novel vectors pLG609-1, pLG609-2 and pLG609-3 respectively as described in FIG. 7, each containing a different reading frame for the Hly A 23 Kd secretion signal region.

The vectors pLG609-1, pLG609-2 and pLG609-3 thereby accommodate the insertion of a second DNA sequence in any of the three reading frames relative to and upstream of the 3' end of hly A.

EXAMPLE 4

Secretion of a Bacterial Outer Membrane Protein Fused to the Hly A C-Terminal Region A. Construction of a lacZ-ompF-hly A Chimeric Gene A chimeric protein containing at the N-terminus 10 amino acids of a β-galactosidase moiety with its translational start signals, a central portion containing the majority of the outer membrane porin OmpF and its C-terminus the secretion signal of Hly A was constructed. As a first step in this construction a lacZ-ompF hybrid gene was made in pUC12 (FIG. 8). The core of the ompF gene, lacking DNA sequences encoding the first 11 amino acids of the N-terminus and the final 30 amino acids of the C-terminus of mature OmpF was removed from pLG361 (Jackson et al 1985 EMBO J. 4 2377-2383) on a 0.9 kb BglII-HincII fragment. This was inserted downstream of the lac promoter of pUC12 which had been digested with BamHI and HincII. The intermediate plasmid pLG631 encoded a chimeric protein containing at its N-terminus the first 10 amino acids of a β-galactosidase moiety fused to the central 300 amino acids of OmpF. Secondly, pLG609 was digested with EcoRI and filled in using Klenow to make blunt ends, before being further digested with HindIII to generate a 1.6 kb fragment. This contained the 3' end of hly A and was inserted into pLG631, which had been digested with HincII and HindIII. The resulting plasmid pLG632 was confirmed by restriction analysis and contained a lacZ-ompF-hly A gene fusion under the control of the lac promoter. Thus, pLG632 was predicted to encode a 56 Kd chimeric protein including the final 218 amino acids of Hly A. Transcription of this gene fusion was under the control of the lac promoter and translation was controlled by the start signals of β-galactosidase.

B. Secretion of the 56 Kd Chimeric Protein into the Medium is Dependent upon the Presence of Hly B and Hly D The 23 Kd C-terminal peptide of Hly A is specifically secreted into the medium from E. coli SE5000 containing the export functions, Hly B and Hly D, (Nicaud et al 1986b FEBS Lett. 204 331-335) encoded by pLG575 (Mackman et al J. Loc. Cit. 1985a). Therefore, we used the same conditions in order to test whether the 56 Kd chimeric protein, including this 23 Kd peptide of Hly A, could be recognised and specifically released into the medium using this system. For comparison, FIG. 9a shows the rapid accumulation of the 23 Kd peptide in the medium of strain SE5000 (pLG575) after derepression of the tac promoter of pLG609 with IPTG.

Proteins were analysed by SDS PAGE and visualised by Coomassie brilliant blue (top panel) or by using polyclonal antibody to Hly A in a Western blot (bottom panel). IPTG was added at t=0h. Cells: track 1, t=0h; track 2, t=2h; track 3, t=3h; track 4, t=4h. Supernatant: track 1, t=0h; track 2, t=2h; track 3, t=3h; track 4, t=4h.

A Western blot (bottom panel) further shows that the vast majority of the 23 Kd protein is indeed in the medium and does not accumulate significantly inside the cells. pLG632 was transformed into strain JM101 F'lacI$^q$ and the lac promoter, upstream of the lacZ-ompF-hly A hybrid gene, was derepressed using IPTG. FIG. 9b shows the induction of the 56 Kd chimeric protein, indentified in a Western blot using polyclonal antibody to Hly A, in the presence and absence of the haemolysin export genes.

Cell and culture supernatant (SN) samples were taken from cultures of E. coli JM101 (pLG632) and E. coli JM101 (pLG632/pLG575) (referred to as −export and +export respectively) at the time of induction with IPTG and 2h post induction. Proteins were analysed by SDS PAGE and visualised using polyclonal antibody to Hly A. The arrow indicates the position of the 56 Kd ompF-hlyAc hybrid. −export: track 1, t=0h (cells); track 2, t=0h (SN); track 3, t=2h (cells); track 4, t=2h (SN), +export: track 5, t=0h (cells); track 6, t=0h (SN); track 7, t=2h (cells); track 8, t=2h (SN).

In the absence of Hly B and Hly D, the 56 Kd protein remained cell associated. However, when the haemolysin export genes were provided by pLG575, the vast majority of the chimeric protein was now detected in the culture medium, with no detectable amounts inside the cells. Clearly, both the 23 Kd peptide of Hly A and the 56 Kd chimeric protein are specifically recognised by the haemolysin export pathway and secreted into the medium. FIG. 9c shows a time course for the accumulation of the 56 Kd chimeric protein in the culture supernatant after induction and the stained profile indicated that, this protein was specifically released into the medium.

A culture of JM101 (pLG632 and pLG575) in L broth was induced with IPTG to derepress the lac promoter. Cell and culture supernatant samples were taken at time of induction and at subsequent intervals. Proteins were analysed by SDS PAGE and visualised by Coomassie blue staining. Molecular weights are indicated in kilodaltons. Cell samples: Track 1, t=0h; Track 2, t=60 min; Track 3, t=120 min; Track 4, t=180 min; Supernatants: Track 5, t=0h; Track 6, t=60 min; Track 7, t=120 min; Track 8, t=180 min.

Although the total amount of protein was less than the 23 Kd C-terminal peptide alone (FIG. 9a), this may simply reflect a higher level of transcription from the tac promoter of pLG609 after induction compared with that of the lac promoter present upstream of the lacZ-ompF-hly A gene fusion on pLG632.

EXAMPLE 5

The Hly A secretion Signal is Located Within the Final 113 Amino Acids of the C-terminus The release of the 23 Kd C-terminal peptide of Hly A indicated that the secretion signal was located within these last 218 residues. Furthermore, deletion of the final 27 amino acids apparently disrupted the signal and abolished secretion of the resulting polypeptide (Gray et al (1986) Mol. Gen. Genet. 205 127-133). Therefore, to more specifically localise the region that was necessary for secretion, two plasmids were constructed which expressed smaller C-terminal fragments of Hly A (FIG. 10). First, a 138 bp DNA fragment encoding 46 amino acids was deleted from within hly A encoded by pLG609. The resulting plasmid, pLG620, contained part of the 3' end of hly A under the control of the tac promoter and expressed an 18 Kd C-terminal fragment of Hly A. Secondly, pLG621 was made by inserting a 353 bp DraI DNA fragment from pLG620 into the vector pUC12 (see FIG. 10). This created a hybrid protein consisting of the first 9 residues of a β-galactosidase moiety fused to the final 113 amino acids of Hly A. This gene fusion was under the control of the lac promoter.

In order to test whether the C-terminal peptides encoded by pLG620 and pLG621 were secreted by the haemolysin export pathway, these plasmids were transformed into JM101 containing pLG575. FIG. 11 shows The secretion of various C-terminal fragments of Hly A using the haemolysin export pathway.

Proteins from culture supernatant (SN) samples were analysed by SDS-PAGE followed by staining with Coomassie brilliant blue. Track 1, SN E. coli JM101 (pLG609/pLG575) Track 2, SN E. coli JM101 (pLG620/pLG575) Track 3, SN E. coli JM101 (pLG621/pLG575) A 14.3 Kd M. wt standard is also shown.

The results show that upon induction both the 18 and 12 Kd peptides encoded by pLG620 and pLG621 respectively were secreted into the medium. This strongly suggested that the secretion signal of the Hly A protein was contained within the final 113 amino acids of the C-terminus. The amount of 12 Kd peptide secreted into the medium was lower than the amount of both 23 and 18 Kd proteins but again this may reflect a lower level of transcription from the lac promoter.

EXAMPLE 6

The final 27 Amino Acids of Haemolysin can allow the Secretion of a Chimeric Protein into the Medium Further information on the minimal sequence containing the Hly A secretion signal was gained by studying the release of chimeric proteins. We have shown that the final 218 amino acids of Hly A can direct the secretion of a 56 Kd chimeric protein composed of OmpF and the C-terminal portion of Hly A into the medium. We show below that a secretion signal is located within the final 113 amino acids. Thus, sequences of hly A were deleted from within the lacZ-ompF-hly A hybrid gene, without altering the lacZ or ompF sequences, to form two hybrid proteins which contained at their C-terminus only an undisturbed block of the final 27 amino acids of Hly A.

A partial restriction map of part of pLG570 is shown in FIG. 10. pLG609 contains a gene fusion between lacZ and the 3' end of hly A which encodes a 23 Kd chimeric protein consisting of 5 residues of β-galactosidase at its N-terminus fused to the final 218 amino acids of Hly A at its C-terminus (Nicaud et al, (1986b) FEBS Lett. 204 331-335). Transcription of this lacZ-hly A hybrid gene is controlled by a tac promoter. pLG620 was made from pLG609 by deleting a 138 bp BalI fragment from within the 3' end of hly A. pLG620 contains a lacZ-hly A hybrid gene, under the control of the tac promoter, which encodes an 18 Kd chimeric protein including 172 residues of Hly A. pLG621 was constructed by inserting a 353 bp DraI fragment, isolated from pLG620, into the SmaI site of the vector pUC12. Recombinants were identified as white colonies by growth on media containing X-gal/IPTG and the orientation of the insert was confirmed by restriction analysis. PLG621 contains a lacZ-hly A gene fusion, under the control of the lac promoter, and encodes a 12 Kd chimeric protein consisting of 9 residues of a β-galactosidase moiety fused to the final 113 amino acids of Hly A.

FIG. 10 also shows a partial restriction map of part of pLG361 (Jackson et al 1985, Embo J. 4 2377-2383). pLG632 was constructed as previously described in FIG. 8 and encodes a 56 Kd chimeric protein. pLG633 and pLG634 were both created by first digesting pLG632 to completion with BglII and removing the sticky ends using S1 nuclease. Secondly, the DNA was partially digested with BalI and the large DNA fragments isolated. After ligation, the DNA was transformed into strain JM101 F'lacI$^q$ and plasmids containing the appropriate deletions were identified by restriction analysis.

Restriction enzymes are as follows: B-BalI, Bg-BglII, D-DraI, E-EcoRI.

The two plasmids generated, pLG633 and pLG634 (FIG. 10) encode chimeric proteins of 45 and 40 Kd respectively. Both these chimeric proteins included the same 27 amino acid region from the extreme C-terminus (see FIG. 12 for amino acid residues in this region). However, in the 45 Kd protein this small C-terminal region was separated from the fusion site with the OmpF portion of the molecule by 98 residues of Hly A, whereas in the 40 Kd protein only 52 residues of Hly A separated this region from the fusion site with OmpF.

Secretion of the 45 and 40 Kd chimeric proteins was tested using JM101 containing pLG575. Cell and supernatant fractions were Western blotted against polyclonal antibody to OmpF since antibody to Hly A does not detect either of these proteins. FIG. 13 shows that upon induction the 45 Kd chimeric protein was secreted into the medium, although the total amount accumulated was less than that of the 56 Kd chimeric protein and small amounts of the 45 Kd protein were found to be cell associated. This result suggested that the last 27 residues of Hly A may in fact contain the majority of the secretion signal and be sufficient to allow some specific secretion through the haemolysin export pathway.

As shown in FIG. 13 strains E. coli JM101 (pLG632/pLG575), E. coli (pLG633/pLG575) and E. coli JM101 (pLG634/pLG575) were induced with IPTG and 2h after induction cell and supernatant (SN) samples were analysed by SDS-PAGE and proteins detected by Western blotting using polyclonal antibody to OmpF. Authentic OmpF is indicated at 36 Kd. Track 1, JM101 cells; track 2, JM101 (pLG634/pLG575) cells; track 3, JM101 (pLG633/pLG575) cells; track 4, JM101 (pLG632/pLG575) cells; track 5, JM101 (pLG634/pLG575) SN; track 6, JM101 (pLG633/pLG575) SN; track 7, JM101 (pLG632/pLG575) SN.

We have examined the final 200 C-terminal amino acids of Hly A and their predicted secondary structure (FIG. 12).

The last 200 amino acids encoded by the 3' end of hly A from pLG570 (Gray et al, (1986) Mol. Gen. Genet. 205 127-133). Open and closed boxed areas indicate predicted regions of weak or stronger α-helical regions respectively.

Interestingly, a potential α-helix was found between residues 167 and 177, a region spanning the BglII site used in the construction of pLG633 and pLG634. This region may serve to separate the proposed 27 amino acid secretion signal from the remainder of the molecule.

Significantly, by examining the fusion sites within the hly A sequences of pLG633 and pLG634, we can see that this potential α-helix is partly recreated in the 45 Kd chimeric protein but not in the 40 Kd chimeric protein. This could explain why significant amounts of the 45 Kd protein are secreted into the medium.

Since the normal Hly secretion mechanism must be post translational it is important that the secretion signal is not buried within the tertiary structure of the polypeptide being transported. Inspection of the predicted secondary structure of the normal Hly A molecule, the smaller truncates of Hly A which are secreted, and the OmpF and prochymosin hybrids indicate that the region of the signal sequence always appears to form a distinct domain of secondary structure separate from the bulk of the molecule. It will be appreciated therefore that although the discrete signal in the C-terminal region of Hly A is sufficient for recognition of the Hly B, D export system, the efficient secretion of particular hybrids may require the insertion of spacer amino acids sufficient to ensure that the signal sequence remains accessible to the Hly B, D secretion machinery.

The use of antibody to OmpF also revealed in FIG. 13 that mature OmpF (36 Kd) was present in the medium in small amounts.

Mug-Opstelten and Witholt (1978 Biochim. Biophys. Acta. 508 287-291) have previously shown that mature OmpF protein is normally released from wild type *E. coli* into the medium in a vesicle associated form. To test whether the 56 Kd chimeric protein was released in the form of vesicles, culture supernatant samples were treated with protease. The 56 Kd hybrid protein was found to be completely degraded by protease whereas the mature OmpF protein, embedded in the membrane of the vesicle, was completely resistant (unpublished data). Moreover, when culture supernatants were sedimented (40 rpm, 4h, 50Ti rotor) the results clearly showed that all the wild type OmpF protein was in the pellet whereas all of the chimeric protein remained in the supernatant (unpublished data). Therefore, secretion of the chimeric protein appears to be specific and does not involve preferential release of portions of the outer membrane.

EXAMPLE 7

Construction and Secretion of Prochymosin-Hly A Hybrids

Figure 1:
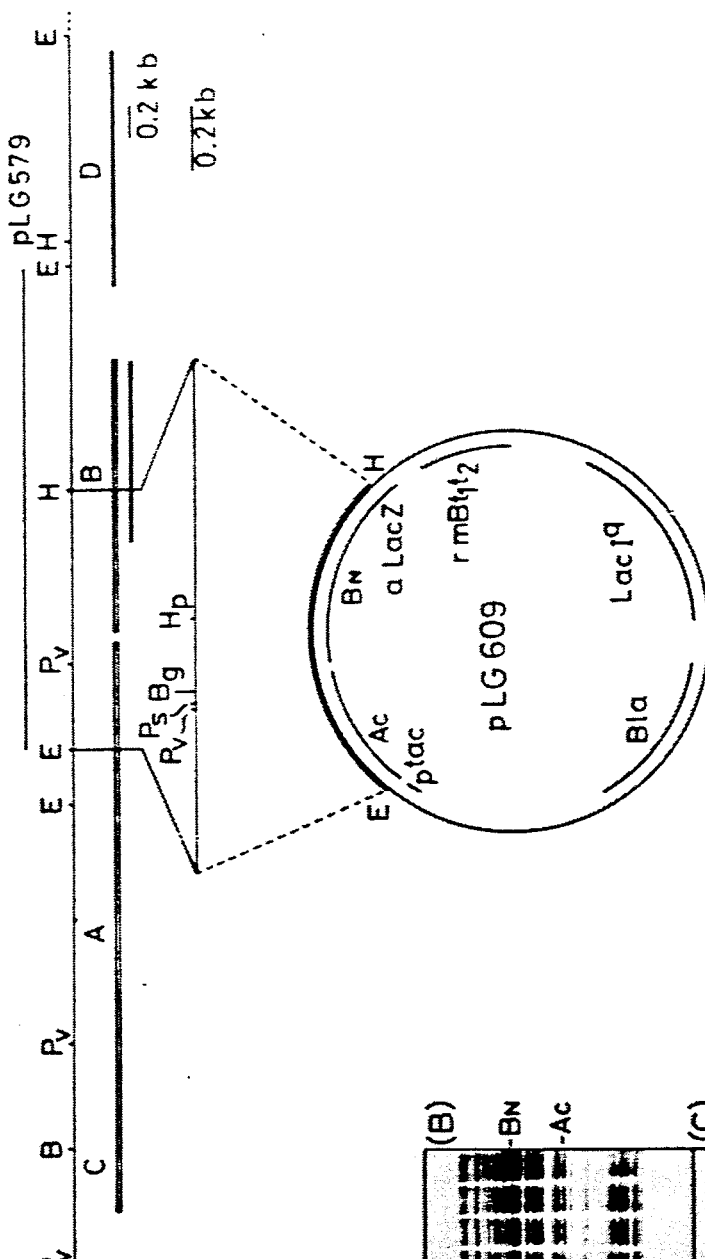
FIG. 1 shows: a restriction site may of pLG570 and plasmid diagram indicating the mode of construction of plasmid pLG609.

The EcoRl-HindIII fragment (FIG. 1) carrying the 3' end of Hly A encoding a 23 Kd protein was cloned into pTTQ18 (FIG. 14) to generate the plasmid pLG609 (FIG. 1). A series of subclones were constructed by inserting various oligonucleotides into the unique EcoRl site of pLG609 to produce different reading frames for the 3' Hly A gene (FIG. 7).

Figure 16B:
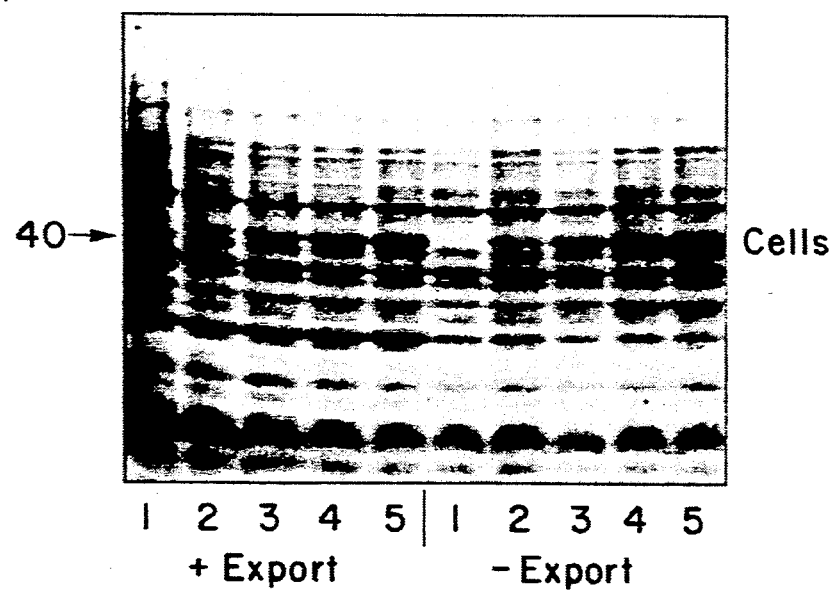

The first prochymosin-Hly A hybrid (to the XmaI site) was constructed as shown in FIG. 15 from the dual origin vector pMG168 (UK Patent No. GB 2136814B) and pLG609-1 to form pPH-1. The 40 Kd product, confirmed by antibody to Hly A was secreted into the medium if the cells contained pLG575 carrying the export genes hly B and hly D. FIG. 16 shows the time course of production of 40K hybrid prochymosin-Hly encoded by pPH-1. To induce high level expression from the trp promoter to transcribe the hybrid gene the culture was shifted to 37° C. This inactivates the λ repressor CI857 leading to extensive transcription of the λ promoter pR which in turn disrupts downstream control of copy number of the vector. Amplification of plasmid number titrates out the trp repressor and then allows high level expression from trp.

In FIG. 16— Track 1-0 min, Track 2-30 min induction, Track 3-60 min induction, Track 4-90 min induction, Track 5-120 min induction.

In order to construct a larger portion of prochymosin (to the ApaI site) fused to the Hly A secretion signal advantage was taken of the availability of the Hly A secretion signal in all three reading frames provided in the pPH plasmid series (FIG. 17). The larger prochymosin hybrid was then constructed from the dual origin vector (pMG168) and pPH-2. The resulting plasmid, encoding a 50 Kd hybrid protein, is pApa-2 which encodes a larger fragment of the prochymosin gene fused to hly A-C-terminal DNA encoding the 23 Kd protein (FIG. 18).

Figure 19B:
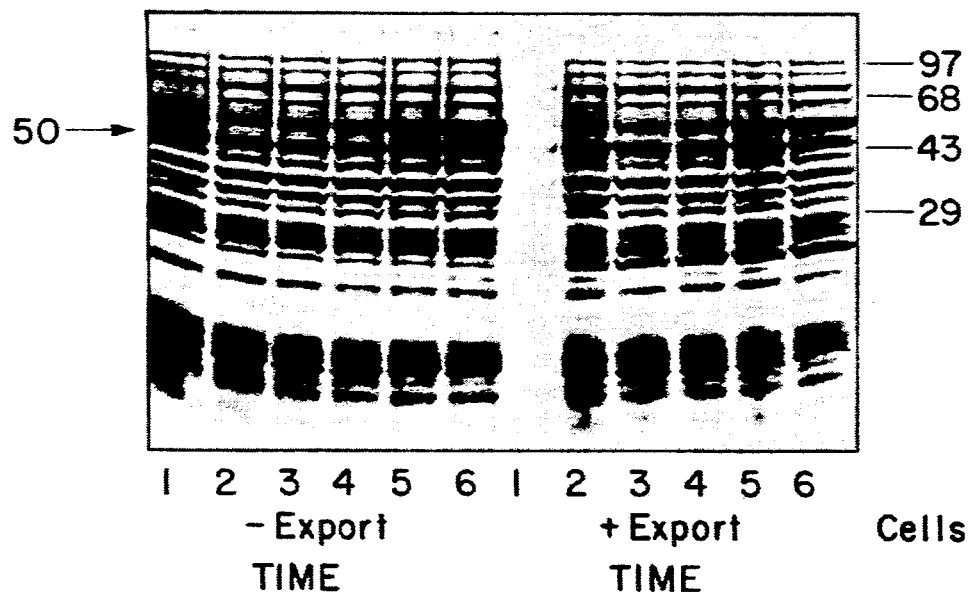

FIG. 19 shows the time course of production of the 50K hybrid prochymosin-Hly encoded by pApa-2. Details as described above for FIG. 16.

The results indicate that this hybrid is secreted provided the export plasmid pLG575 is also present. The identity of the hybrid was confirmed using antiserum to both prochymosin and Hly A.

We claim:

1. A DNA sequence coding for a fusion protein comprising a first polypeptide and a further peptide in which the further peptide comprises a C-terminal secretion sequence.

2. A DNA sequence according to claim 1 wherein the fusion protein is a C-terminal fusion protein.

3. A DNA sequence according to claim 1 wherein the further peptide comprises a haemolysin C-terminal secretion sequence.

4. A vector comprising a DNA sequence according to claim 1.

5. Host cells transformed or transfected with a vector according to claim 4.

6. An expression vector containing a first DNA sequence coding for a peptide comprising a haemolysin C-terminal secretion sequence and a unique restriction site positioned relative thereto in such a way that expression of a fusion protein comprising the peptide and a further peptide may be obtained when a second DNA sequence coding for the polypeptide is inserted at the unique restriction site.

7. A process for the production of a polypeptide, in which host cells, which express transport proteins effective to secrete a peptide comprising a C-terminal secretion sequence, transformed or transfected with DNA coding for a fusion protein comprising the polypeptide and a further peptide comprising a C-terminal secretion sequence are cultured to express and secrete the fusion protein.

8. A process according to claim 7 wherein following secretion, the fusion protein is cleaved to yield the polypeptide.

9. A process according to one of claims 7 or 8 wherein the transport proteins are haemolysin C-terminal secretion system transport proteins.

10. A process according to claim 7 or claim 8 wherein the C-terminal secretion sequence is a haemolysin C-terminal secretion sequence.

11. A process according to claim 10 wherein the transport proteins are haemolysin C-terminal secretion system transport proteins.

* * * * *